(12) United States Patent
Franzini et al.

(10) Patent No.: US 6,509,324 B1
(45) Date of Patent: Jan. 21, 2003

(54) CHELATING COMPOUNDS, THEIR COMPLEXES WITH PARAMAGNETIC METALS

(75) Inventors: Maurizio Franzini, Milan (IT); Andrea Beltrami, Milan (IT); Luisella Calabi, Milan (IT); Alessandro Maiocchi, Milan (IT); Mario Virtuani, Milan (IT); Pier Lucio Anelli, Milan (IT); Kondareddiar Ramalingam, Dayton, NJ (US); Ramachandran S. Ranganathan, Princeton, NJ (US)

(73) Assignee: Bracco S.p.A., Milan (IT)

( * ) Notice: Subject to any disclaimer, the term of this patent is extended or adjusted under 35 U.S.C. 154(b) by 0 days.

(21) Appl. No.: 09/913,711

(22) PCT Filed: Dec. 20, 2000

(86) PCT No.: PCT/EP00/12977

§ 371 (c)(1),
(2), (4) Date: Sep. 24, 2001

(87) PCT Pub. No.: WO01/46207

PCT Pub. Date: Jun. 28, 2001

(30) Foreign Application Priority Data

Dec. 21, 1999 (IT) .......................................... MI99A2656

(51) Int. Cl.⁷ ............................ C07F 9/28; A61K 31/66
(52) U.S. Cl. ........................ 514/102; 514/107; 514/114; 562/11; 562/12; 562/14; 562/15
(58) Field of Search .............................. 562/14, 11, 12, 562/15; 514/102, 107, 114

(56) References Cited

U.S. PATENT DOCUMENTS

| | | | |
|---|---|---|---|
| 4,073,700 A | * | 2/1978 | Weisberg et al. |
| 4,647,447 A | * | 3/1987 | Gries et al. |
| 5,039,512 A | | 8/1991 | Kraft |

FOREIGN PATENT DOCUMENTS

| | | |
|---|---|---|
| GB | 1 392 242 | 4/1975 |
| GB | 2 137 612 | 10/1984 |
| IT | WO 98/05625 A1 * | 2/1998 |
| WO | WO00/30688 | 6/2000 |

OTHER PUBLICATIONS

Adzamli et al, Development of Phosphonate Derivatives of Gadolinium Chelates for NMR Imaging of Calcified Soft Tissues, 1989, Journal of Medicinal Chesostry, 32,pp. 139–144.*

Szot et al, Efficiency of Diethylentriaminedicarboxytriphosphnic Acid in Removing Internally Deposited Plutonium–239 in Mice, 1981, Nukleonika, 26(4–5–6), pp. 729–733.*

* cited by examiner

*Primary Examiner*—Johann Richter
*Assistant Examiner*—Paul A. Zucker
(74) *Attorney, Agent, or Firm*—Nixon & Vanderhye P.C.

(57) ABSTRACT

Compounds able to chelate bi- and trivalent paramagnetic metal ions, their chelated complexes with these metal ions and physiologically compatible salts thereof and therein magnetic resonance imaging.

30 Claims, No Drawings

CHELATING COMPOUNDS, THEIR COMPLEXES WITH PARAMAGNETIC METALS

This application is a 371 of PCT/EP00/12977 filed Dec. 20, 2000.

This invention refers to new compounds which can chelate paramagnetic bi- and trivalent metal ions, their chelates with said metal ions and their use as contrast agents in magnetic resonance imaging (M.R.I.).

From a radiologist's point of view, an improvement in the radiographic image, which means a better contrast enhancement between healthy and diseased tissues, is seen as an aid to the diagnosis which can be obtained through previous administration of suitable exogenous substances.

These substances cause a significant alteration of a specific characteristic, known as relaxivity, of the water protons belonging to the tissue under examination, when such protons are submitted to an external magnetic field.

These substances are known as contrast agents for M.R.I. A number of chelated complexes of linear and cyclic polyaminopolycarboxylic ligands with paramagnetic metals are known to be useful as M.R.I. contrast agents.

Said compounds generally derive from the two basic polyaminopolycarboxylic structures, namely diethylenetriaminopentaacetic acid (DTPA) and 1,4,7,10-tetraazacyclododecane-1,4,7,10-tetraacetic acid (DOTA).

The compounds of the present invention are novel polyamino derivatives comprising at least one phosphonic residue as one of the binding site in the chelating agent structure.

Relaxivity ($r_{1p}$) is an intrinsic property of paramagnetic complexes which characterizes their ability to increase the nuclear magnetic relaxation rate of vicinal protons. In the case of Gd(III) chelates with $q \geq 1$, wherein q is the number of coordinated water molecules, a remarkable contribution to the increase in relaxation observed for water protons of the solvent derives from the exchange between the molecule (s) of bound water and the molecules of the remaining solvent (S. Aime et al., Chem. Soc. Rev., 1998, 27, 19).

This contribution ($r_{1p}^{is}$) is related to the relaxation time ($T_{1M}$) and to the residence time ($\tau_M$) of the protons of the water molecule(s) which are coordinated in the inner coordination sphere according to the following equation:

$$r_{1p}^{is} = \frac{1.8 \cdot 10^{-5} q}{(T_{1M} + \tau_M)}$$

$T_{1M}$ receives contributions from the reorientation of the paramagnetic species, $\tau_R$, through the residence time of the coordinated water protons, $\tau_M$, and the electronic relaxation time of the metal ion, $\tau_S$. Moreover, $r_{1p}^{is}$ is the highest when $T_{1M} \gg \tau_M$ (fast exchange conditions) and $T_{1M}$ is as short as possible.

A remarkable increase in $r_{1p}$ at the magnetic field values conventionally used in clinical practice has been up to now obtained, in different ways, mainly by decreasing molecular tumbling, with a consequent increase in $\tau_R$. The expected increase in $r_{1p}$ has not, however, been observed due to the limiting effect caused by the residence time of water molecules, $\tau_M$. A fine tuning of this parameter has become the primary object of current research in the M.R.I. field, as only $\tau_M$ values of about 30 ns would make it possible to completely exploit the decrease in $T_{1M}$ induced by the increase in $\tau_R$. For this reason, the exchange rate values of water molecules in lanthanide (III) complexes are of paramount importance in the development of novel M.R.I. contrast agents. In fact, the residence time of the water molecule(s) coordinated to a Gd(III) complex plays a particularly important role, in that it directly contributes to the nucleus-electron dipolar interaction and controls the transfer efficiency of the paramagnetic effect to the water molecules of the solvent.

The above cited prior art contrast agents, generally comprising polyaminopolycarboxylic acid derivatives, have shown $\tau_M$ values generally comprised between 200 and 2500 ns, where such values are significantly higher than the 30 ns optimum one.

Optimization and harmonization of the above parameters are still remarkably important objects for everyone dealing with the development of novel M.R.I. contrast agents.

The present invention relates to polyamino derivatives comprising as the binding site in the structure of the chelating agent at least one phosphonic is residue, capable of causing an increase in the proton exchange rate and therefore advantageously low $\tau_M$ values.

More particularly, the object of the present invention is acyclic polyamino derivative chelating agents of formula (I), both in the racemic and the optically active forms,

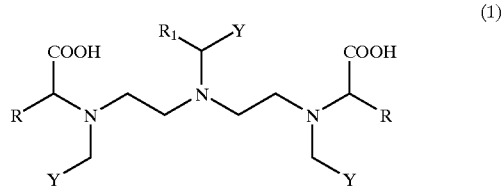

wherein
Y is a COOH group or a PO(OH)$_2$ group, with the proviso that at least one Y group is =PO(OH)$_2$;
R is a hydrogen atom, or —(CH$_2$)$_m$—O—R$_2$, (C$_1$–C$_5$)-alkyl-(C$_6$–C$_{10}$)-aryl or (C$_1$–C$_5$)-alkyl-heteroaryl whose aryl or heteroaryl moiety comprises 1 or 2 fused rings optionally substituted with one or more halogen atoms, OH groups, alkyl(C$_1$–C$_5$) groups and/or an OR$_3$ group, wherein
R$_2$ is (C$_1$–C$_5$)-alkyl-(C$_6$–C$_{10}$)-aryl, optionally substituted with one or more halogen atoms, OH and (C$_1$–C$_5$)-alkyl groups;
R$_3$ is (C$_6$–C$_{10}$) aryl optionally substituted with one or more halogen atoms, OH and/or (C$_1$–C$_5$)-alkyl groups;
m ranges from 1 to 5;
R$_1$ can have the same meanings as R with the proviso that when Y is PO(OH)$_2$, R$_1$ is selected from H, (CH$_2$)$_m$NH$_2$, (CH$_2$)$_m$COOH or an amido derivative thereof.

A further object of the invention are the chelates of said compounds of formula (I) with the bi- and trivalent ions of metal elements having atomic number ranging between 20 and 31, 39, 42, 43, 44, 49, or between 57 and 83, as well as the salts thereof with physiologically compatible organic bases selected from primary, secondary, tertiary amines or basic amino acids, or with inorganic bases whose cations selected from sodium, potassium, magnesium, calcium or mixtures thereof.

A further object of the present invention is the use of the compounds of formula (I), their complexes with paramagnetic metals and the physiologically compatible salts thereof for the preparation of pharmaceutical formulations for the imaging of organs and/or tissues of the human or animal body, by use of M.R.I.

Examples of $(C_1–C_5)$-alkyl-$(C_6–C_{10})$-aryl groups comprise benzyl, phenethyl, naphthylmethyl wherein the aryl moiety is optionally substituted with one or more halogen atoms or $OR_3$ groups wherein $R_3$ is as defined above.

Examples of $(C_1–C_5)$-alkyl-heteroaryl groups comprise pyridylmethyl or indolylmethyl.

Examples of $(C_6–C_{10})$ aryl groups comprise phenyl or naphthyl optionally substituted with one or more halogen atoms, OH and/or $(C_1–C_5)$-alkyl groups.

Examples of $(C_1–C_5)$ alkyl groups preferably comprise methyl, ethyl, isopropyl.

Preferred are compounds of formula (II),

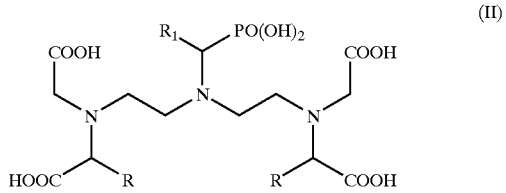

(II)

wherein 4 side carboxylic groups and a central phosphonic group are present and wherein
R and R have the above defined meanings.

Among compounds of formula (II), particularly preferred are those in which $R_1$ is an hydrogen atom and R can assume all previously defined meanings.

Also preferred are the compounds of formula (III)

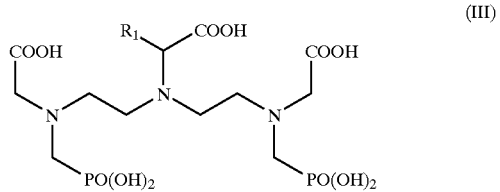

(III)

wherein two side phosphonic groups and three carboxylic groups are present, and wherein
$R_1$ has all the values defined above, as well as the compounds of general formula (IV),

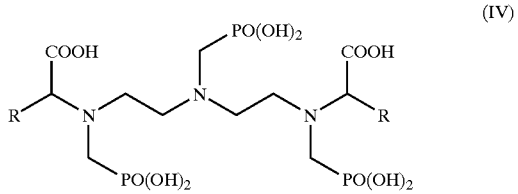

(IV)

wherein three phosphonic groups and two carboxylic groups are present and wherein R has the values defined above.

Particularly preferred are the following compounds:

N,N'-[(Phosphonomethylimino)di-2,1-ethanediyl]bis[N-carboxymethyl-L-phenylalanine];

[[4S-(4R*,12R*)]-4-Carboxy-5,11-bis(carboxymethyl)-1-phenyl-12-[(phenylmethoxy)methyl]-8-(phosphonomethyl)-2-oxa-5,8,11-triazatridecan-13-oic] acid;

N,N'-[(Phosphonomethylimino)di-2,1-ethanediyl]bis[N-carboxymethyl-L-tryptophan];

N,N-Bis[2-[(carboxymethyl)(phosphonomethyl)amino] ethyl]-O-(4-hydroxyphenyl)-3,5-diiodo-L-tyrosine;

N,N'-[(Phosphonomethylimino)di-2,1-ethanediyl]bis[N-(carboxy-methyl)-glycine];

N,N'-[(Phosphonomethylimino)di-2,1-ethanediyl]bis[N-(phosphonome-thyl)glycine];

N,N'-[[[3-Carboxy-1-phosphonopropyl]imino]di-2,1-ethanediyl]bis[N-(carboxymethyl)glycine];

4-Phenyl-N-[trans-4-[[[4-[bis[2-[bis(carboxymethyl)amino] ethyl]amino]-1-oxo-4-phosphonobutyl]amino]methyl] cyclohexylcarbonyl]-L-phenylalanina;

(3β, 5β, 7α, 12α)-3-[[4-[bis[2-[bis(carboxymethyl)amino] ethyl]amino]-1-oxo-4-phosphonobutyl]amino]-7,12-dihydroxycholan-24-oic acid;

N,N'-[[[3-Amino-1-phosphonopropyl]imino]di-2,1-ethanediyl]bis[N-(carboxymethyl)glycine];

as well as the paramagnetic chelated complexes thereof and the physiologically compatible salts thereof.

Preferred chelates are those in which the bi- or trivalent metal ion is selected from $Gd^{(3+)}$, $Dy^{(3+)}$, $Fe^{(3+)}$, $Fe^{(2+)}$ and $Mn^{(2+)}$. Particularly preferred are $Gd^{(3+)}$ chelates.

Preferred cations of inorganic bases optionally suitable for salifying the chelated complexes of the invention particularly comprise the ions of alkali or alkaline-earth metals such as potassium, sodium, calcium, magnesium, and mixtures thereof.

Preferred cations of organic bases suitable for this purpose comprise, inter alia those obtained by protonation of primary, secondary and tertiary amines such as ethanolamine, diethanolamine, morpholine, glucamine, N-methylglucaimine, N,N-dimethylglucarmine.

Preferred cations of amino acids comprise, for example, those of lysine, arginine or ornithine.

The introduction of at least one phosphonic group as the binding site in the structure of the chelating agent unexpectedly provided contrast agents having an advantageous increase in the proton exchange rate and, therefore, particularly low $\tau_M$ values.

In particular, the chelated complexes of the invention are characterized by $\tau_M<100$ ns values, preferably values between 10 and 100 ns, most preferably between 20 and 50 ns.

Among the various synthetic approaches to the compounds of the invention, the one preferred for the preparation of the compounds of formula (II), and particularly for the compounds in which $R_1$ is =H and R has the meanings defined above in claim 1, is reported in the following Scheme 1:

SCHEME 1

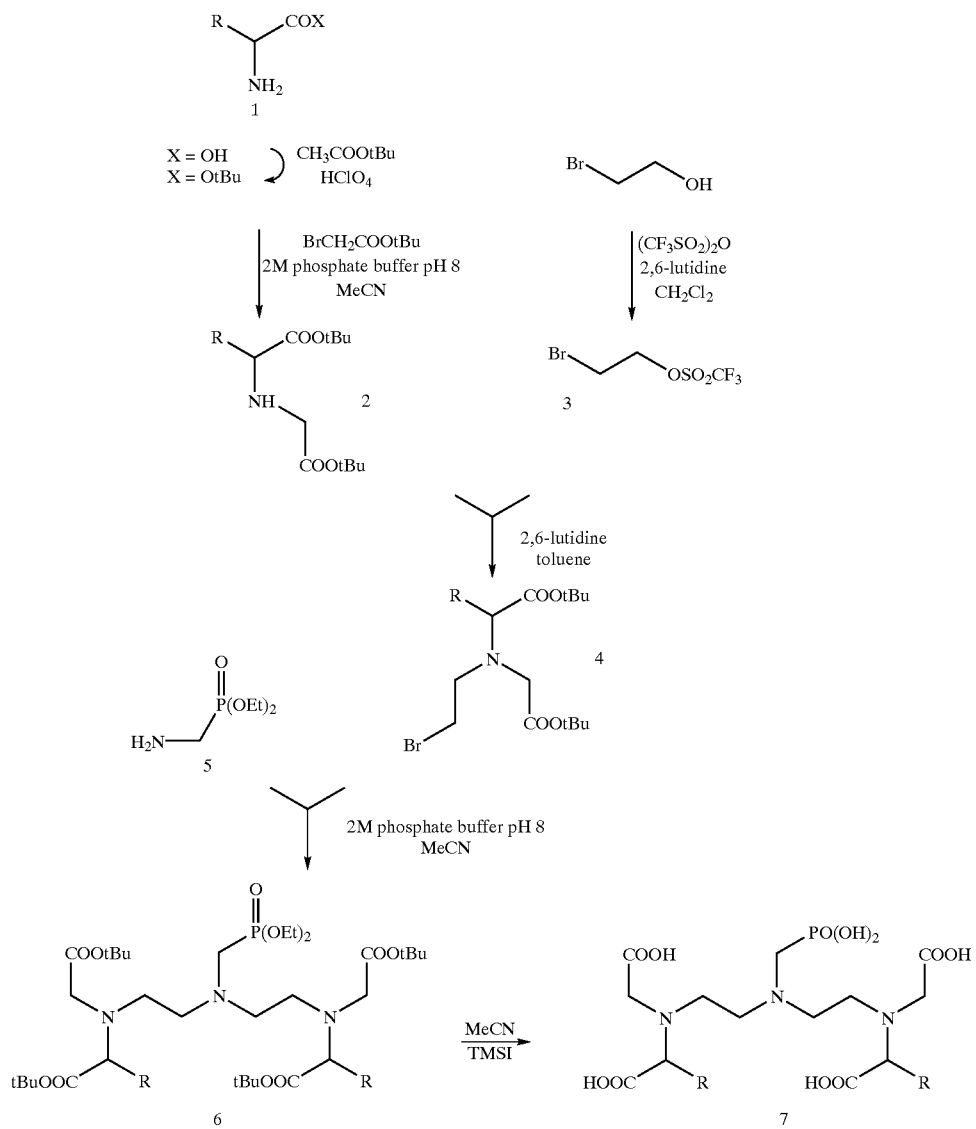

wherein R has the values defined above for compounds (I).

Briefly, the synthetic process of Scheme 1 comprises the following steps:

a) Esterification of a suitable amino acid. Said esterification can be advantageously carried out by reacting the amino acid with an alkyl acetate and an acid such as HClO$_4$. In a variation of the process, the amino acid, previously N-protected by reaction with CBZCl, can be esterified by reaction with an alkyl halide, in the presence of a base such as K$_2$CO$_3$;

b) N-Alkylation of the resulting ester (intermediate 1) by reacting it with a suitable bromoacetate, such as tert-butyl bromoacetate. Said reaction is carried out in an organic solvent preferably selected among acetonitrile, THF, EtOAc and in the presence of a pH 8 buffer solution;

c) Bromoalkylation of the intermediate 2 by reacting it with trifluoromethanesulfonic acid 2-bromoethyl ester (intermediate 3) previously prepared from bromoethanol, trifluoromethanesulfonic anhydride and 2,6-lutidine. The bromoalkylation is carried out in an organic solvent suitably selected among, for example, toluene, acetonitrile, dichloroethane, and in the is presence of an amine selected among ethylenediamine, diisopropylethylamine, triethylamine, to give the intermediate 4. In a variation of the process of the invention, compound 4 can be alternatively prepared starting from the corresponding N-(2-hydroxyethyl) derivative, obtained as described in WO 98/05625, (incorporated herein by reference in its entirety), by reacting it with a brominating agent such as NBS, in the presence of triphenylphosphine;

d) Preparation of aminomethylphosphonic acid diethyl ester (intermediate 5) by direct condensation of tribenzylhexahydrotriazine with a suitable dialkyl phosphite and subsequent debenzylation by catalytic hydrogenation of the condensation product;

e) Bis alkylation of intermediate 5 by reaction with intermediate 4 and isolation of hexaester 6. In the process of the invention, the bis alkylation reaction is preferably carried out in an organic solvent such as acetonitrile, ethyl acetate, and in the presence of a pH 8 buffer solution;

f) Deprotection of the acidic functions of intermediate 6 and isolation of the acid chelating agent 7. Said deprotection can be obtained by reacting the hexaester with iodotrimethylsilane in an organic solvent, such as $CH_3CN$.

A different synthetic approach for the preparation of the compounds of formula (II) in which, on the contrary, R is =H and $R_1$ has the meanings defined above in claim 1, is reported in the following Scheme 1 bis:

SCHEME 1bis

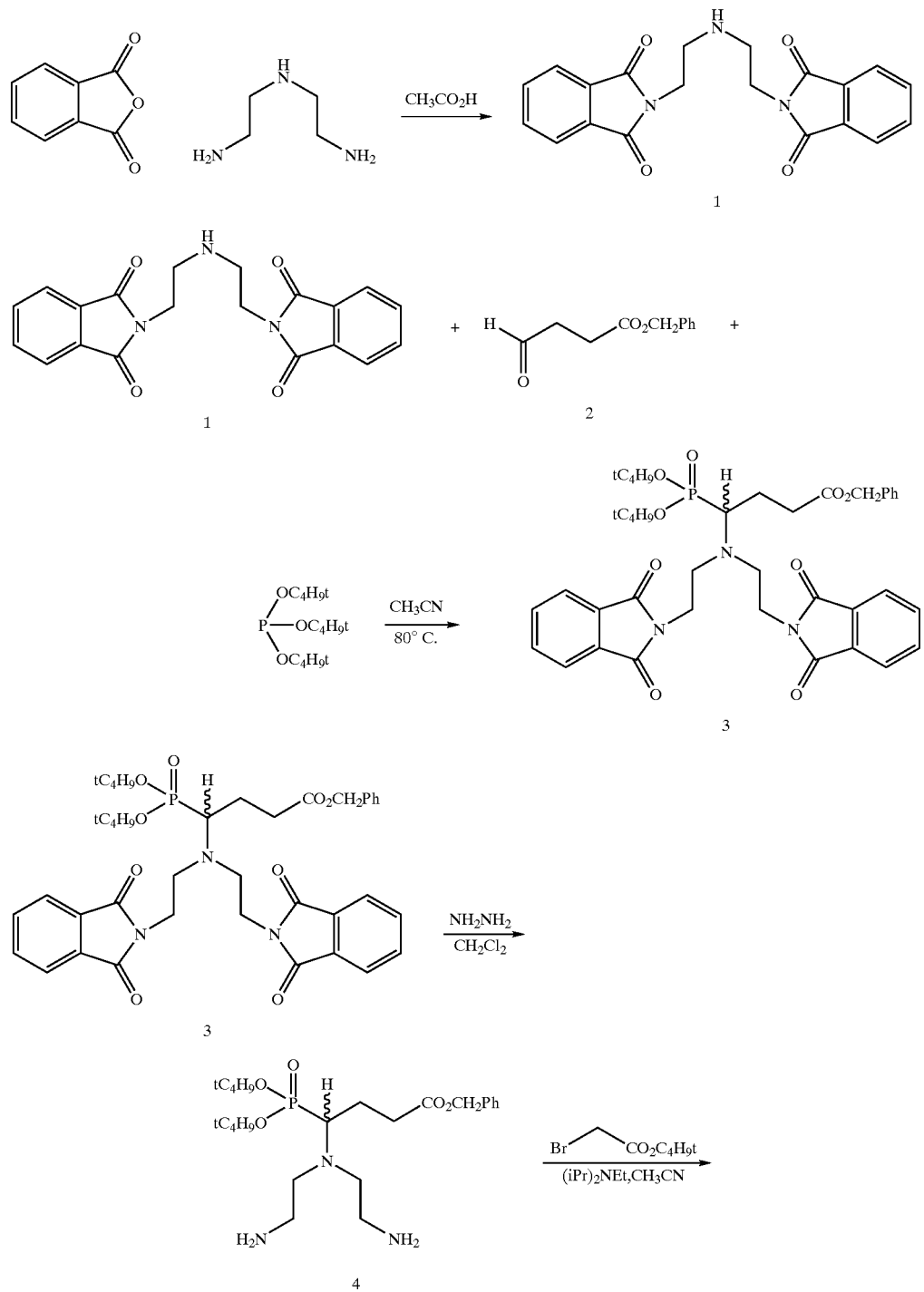

-continued
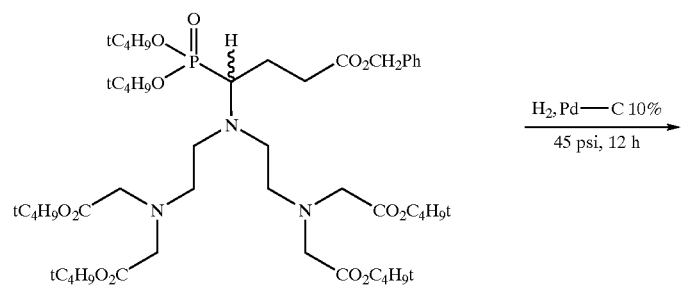
5
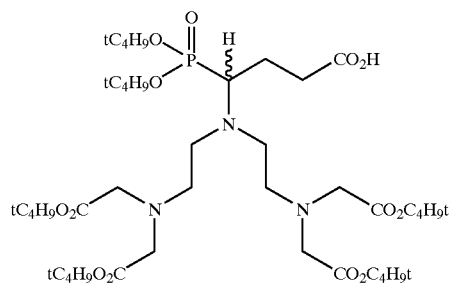
6
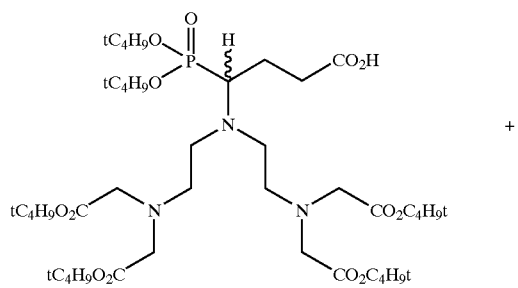
6 +
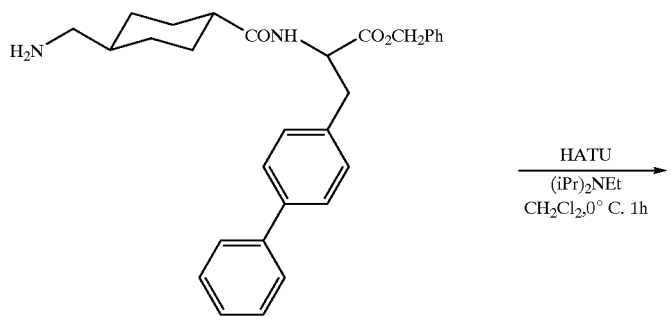
7

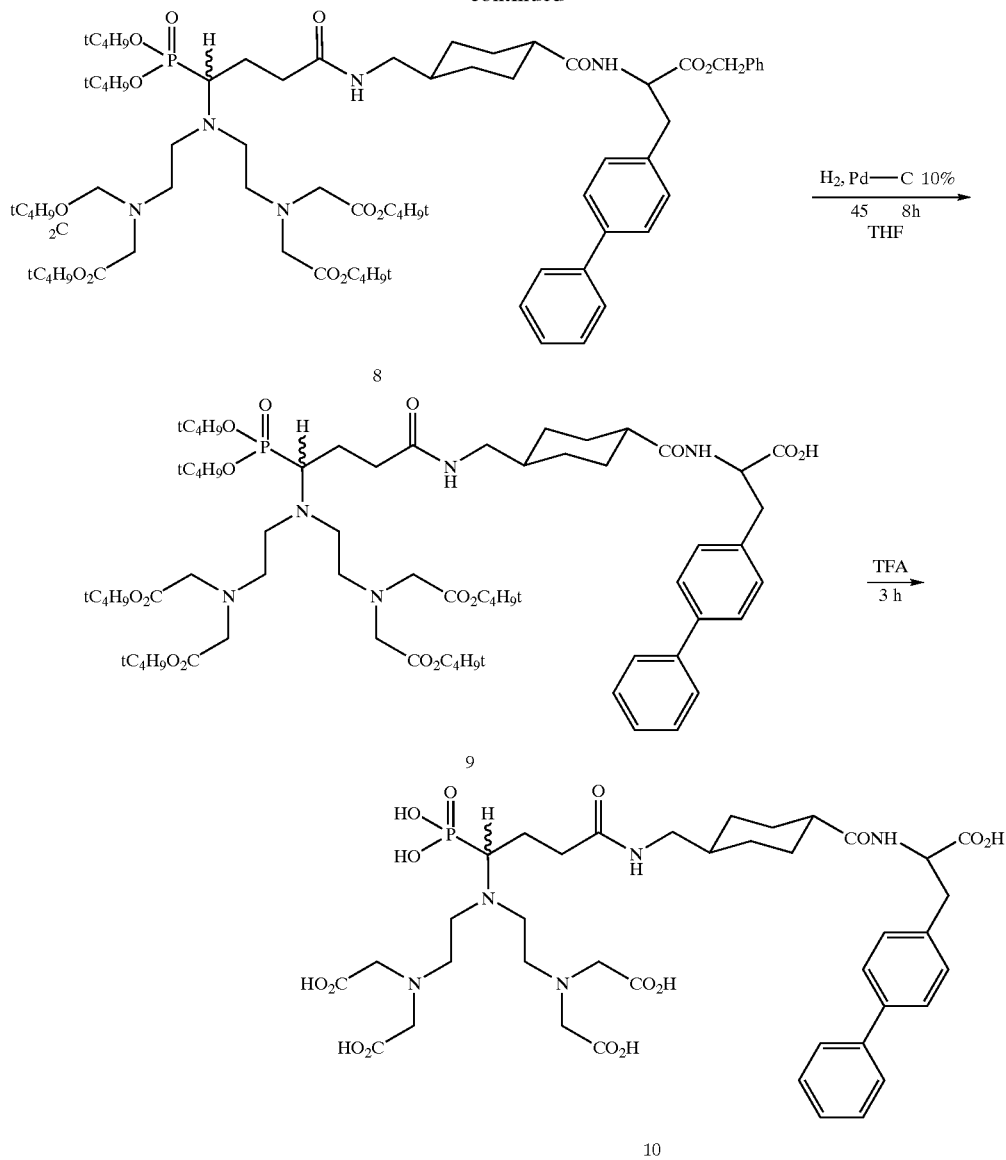

in which, as an example, is detailed the preparation of one of several preferred complex compounds of the invention.

The synthetic process of SCHEME 1bis essentially comprises the following steps:

a) Preparation of 2,2'-(Iminodi-2,1-ethanediyl)bis-1H-isoindole-1,3(2H)-dione) (intermediate 1) by reacting phthalic anhydride with diethylenetriamine in acetic acid;

b) N-alkylation of the bis-phthalimido derivative 1 by reacting it with 3-benzyloxycarbonylpropionaldehyde (intermediate 2) in a suitable organic medium, and then with tris(tert-butyl) phosphite to give intermediate 3;

c) Removal of phthalic groups to give corresponding diamine (intermediate 4) by reaction, for example, with hydrazine;

d) N-alkylation of the diamine 4 by reaction with a suitable halo acetate, such as, for example, tert-butyl bromoacetate, to give intermediate 5. This reaction is carried out in an organic solvent preferably selected from acetonitrile, ethyl acetate, and in the presence of a suitable tertiary amine such as, for example, diisopropylethylamine;

e) Debenzylation by catalytic hydrogenation of the intermediate 5 and isolation of the hexaester monocarboxylic acid 6. In a preferred process this hydrogenation is carried out in an organic solvent such as, for example, THF and catalysed by 10% Pd-C;

f) reaction of the hexaester monocarboxylic acid 6 with a suitable amino compound (compound 7) and isolation of the corresponding amide (derivative 8). In a preferred process said reaction is performed in presence of HATU (O-(7-Azabenzotriazol-1-yl)-N,N,N',N'-tetramethyluronium hexafluoro-phosphate);

g) Deprotection of the acidic functions of the hexaester and recovery of the acid chelating agent (compound 10). In one preferred process of the invention the deprotection of the acidic functions is performed on the hexaester derivative prepared at step e) (intermediate 6) to give, for example, the acid chelating agent of EXAMPLE 7, disclosed later on in the experimental section of the invention. In the process of Scheme 1 bis, otherwise, the deprotection includes a first debenzylation step, by catalytic hydrogenation, of the benzylester On the other hand, compounds of general formula (III) are preferably prepared according to the following Scheme 2

SCHEME 2

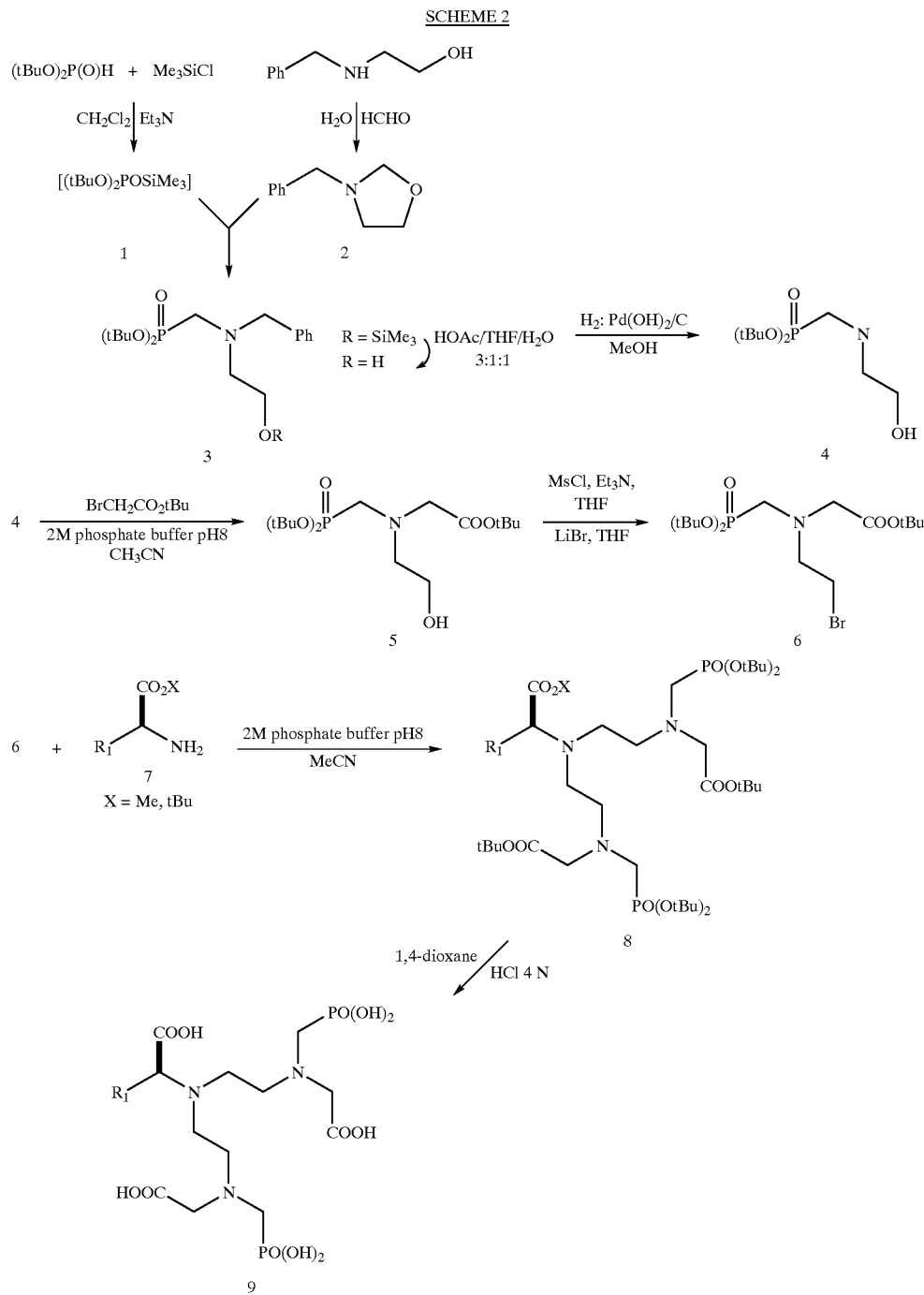

contained in the amido derivative 8 and a second step, including the deprotection of the residual acidic functions of the hexaester 9, to give the chelating agent 10. The hydrogenation is preferentially carried out in an organic solvent such as, for example, THF and catalysed by 10% Pd-C. The subsequent deprotection can be performed, for example, by reacting the hexaester 9 with trifluoroacetic acid.

wherein $R_1$ has the values defined above for compounds (I).

The synthetic process of Scheme 2 comprises the following steps:

a) Preparation of aminomethylphosphonic acid bis tert-butyl ester (bis N-alkyl) derivative (intermediate 3) by reacting bis tert-butyl phosphite, suitably activated (intermediate 1), with aminal (intermediate 2). In particular, in the process of the invention, the phosphonic acid tert-butyl ester is advantageously activated for example with $Me_3SiCl$ in a reaction carried out in organic solvent and in the presence of an amine, such as triethylamine. The resulting trimethylsilyl derivative is reacted with intermediate 2 obtained from 2-benzylaminoethanol and aqueous formaldehyde. This reaction is activated by the presence of a catalytic amount of a lanthanide triflate. Particularly preferred is ytterbium triflate. In the process of the invention, the resulting trimethylsilyl derivative is not isolated but it is directly transformed into the corresponding hydroxy derivative by treatment with a suitable aqueous acid, such as aqueous acetic acid.

b) Catalytic hydrogenation of intermediate 3. In the preferred process this reaction is carried out in alcoholic medium and catalyzed by $Pd(OH)_2/C$.

c) N-alkylation of the resulting compound from step b), (intermediate 4), by reacting it with a suitable haloacetate, such as tert-butyl bromoacetate. This reaction is carried out in an organic solvent preferably selected from acetonitrile, ethyl acetate, and in the presence of a buffer solution pH 8.

d) Transformation of the isolated aminoalcohol (intermediate 5) into the corresponding bromo derivative by reacting it with methanesulfonyl chloride and a brominating agent such as lithium bromide. This reaction is carried out in an organic solvent selected from THF, acetonitrile, ethyl acetate, under nitrogen atmosphere and in the presence of an amine selected from triethylamine, diisopropylethylamine, at temperatures ranging from 20 to $-5°$ C.

e) Condensation of the bromo derivative (intermediate 6) with a convenient amino acid suitably esterified (intermediate 7) and isolation of the polyester (intermediate 8). Said reaction is advantageously carried out in an organic solvent preferably selected from acetonitrile, THF, ethyl acetate and in the presence of a buffer solution pH 8.

f) Deprotection of the acidic functions of the polyester and isolation of the chelating agent (compound 9). The deprotection is, for example, obtained by reacting the polyester with an acid selected from HCl, $H_2SO_4$, in an aqueous mixture of an organic solvent such as dioxane.

The compounds of this invention have a wide range of applications, since they can be used for intravasal, (for instance i.v., intraarterial, intracoronaric, intraventricular administration and so on), intrathecal, intraperitoneal, intralymphatic and intracavital administrations. Furthermore, the compounds are suitable for the oral or enteral administration, and therefore, specifically for the imaging of the gastrointestinal tract.

For the parenteral administration they can preferably be formulated as sterile aqueous solutions or suspensions, whose pH can range from 6.0 to 8.5.

These aqueous solutions or suspensions can be administered in concentrations ranging between 0.002 and 1.0 M. These formulations can be lyophilized and supplied as they are to be reconstituted before use.

For the gastrointestinal use or for injection in body cavities, these agents can be formulated as a solution or suspension optionally containing suitable excipients in order, for example, to control viscosity.

For the oral administration, they can be formulated according to preparation methods routinely used in the pharmaceutical technique or as coated formulations to gain additional protection against the stomach acidic pH, thus preventing the chelated metal ion from release, which takes place particularly at the pH values typical of gastric juices.

Other excipients, such as sweeteners and/or flavouring agents, can also be added, according to known techniques of pharmaceutical formulations.

The solutions or suspensions of the compounds of this invention can also be formulated as aerosols to be used in aerosol-bronchography and instillation.

The compounds of the present invention can optionally be chemically conjugated to suitable macromolecules, targeting vectors or inglobated into suitable carriers.

For example they can also be encapsulated in liposomes or they can be constituents of their chemical structure and used as uni- or multilamellar vesicles.

A non-limiting list of preferred compounds of the invention is reported in the following, to better exemplify the wide applicative potential of the invention.

COMPOUND 1

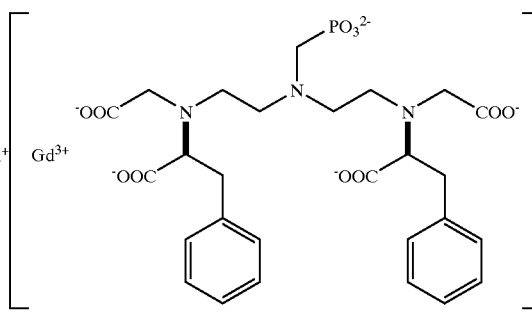

COMPOUND 2

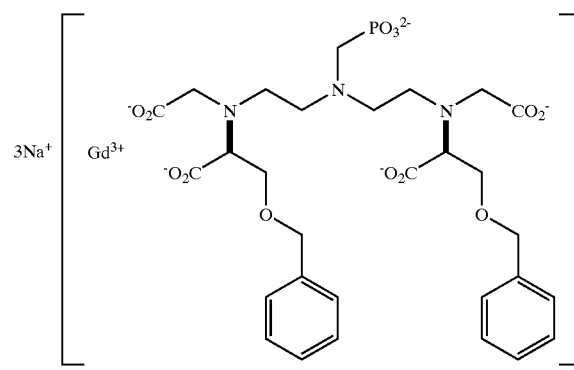

COMPOUND 3

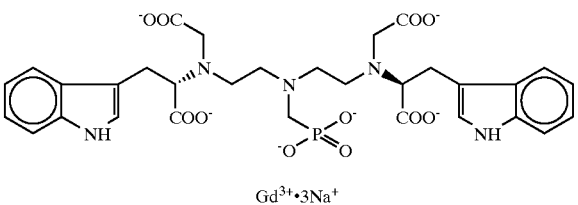

COMPOUND 4
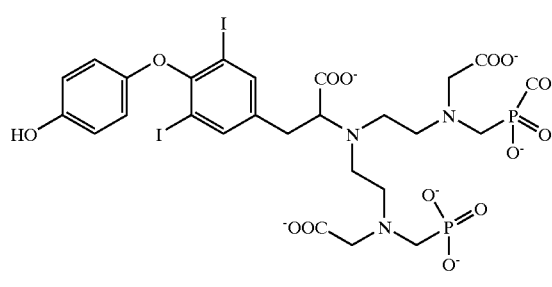
COMPOUND 8
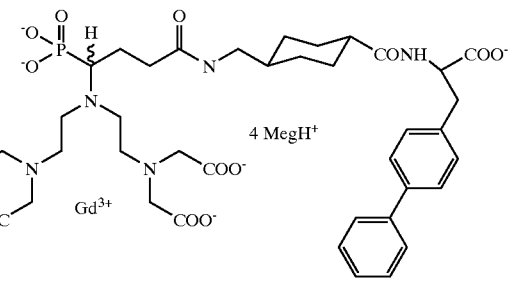
COMPOUND 5
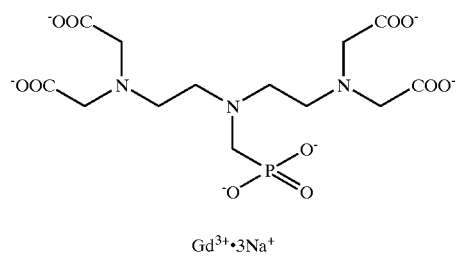
COMPOUND 9
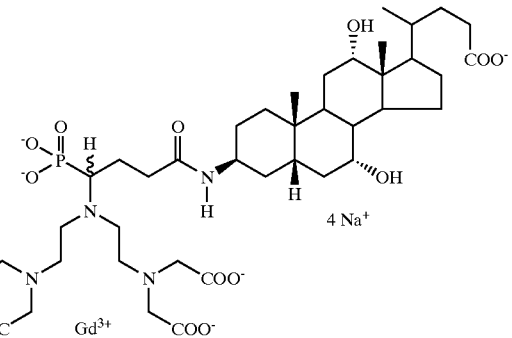
COMPOUND 6
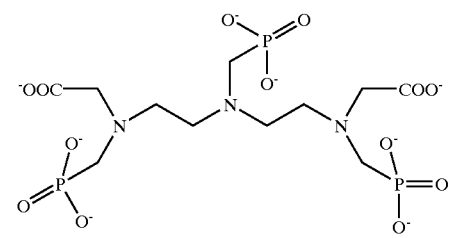
COMPOUND 10
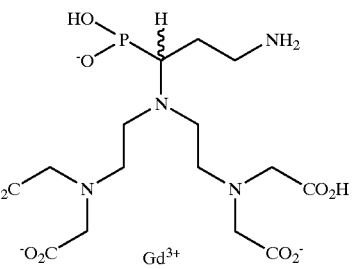
EXPERIMENTAL SECTION
EXAMPLE 1
Gadolinium Complex of [N,N'-[(Phosphonomethylimino)di-2,1-ethanediyl]bis[N-carboxymethyl-L-phenylalamine] Salified with Na (1:3)
COMPOUND 7
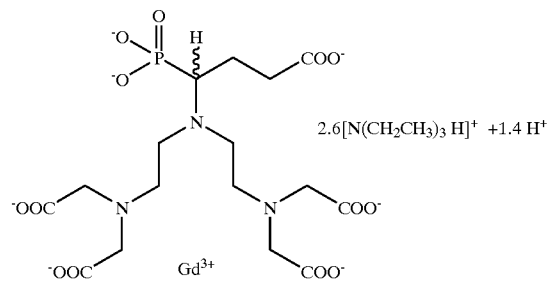
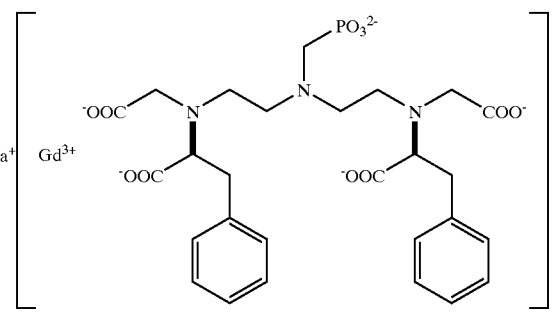

A) L-Phenylalanine 1,1-Dimethylethyl Ester

A solution of L-phenylalanine (62.6 g; 379 mol) in tert-butyl acetate (320 mL) cooled on an ice bath and stirred vigorously is slowly added with 70% aqueous $HClO_4$ (35 mL, 407 mol). After stirring for 11 days at room temperature, the mixture is diluted with 100 mL of water and cooled on an ice bath. The mixture is basified with 5 N NaOH to precipitate a white solid (unreacted phenylalanine) which is filtered off. The mixture is then extracted with EtOAc (4×200 mL), the organic phases are combined and washed with water (2×200 mL) and 5% $Na_2CO_3$ (300 mL). After drying over $Na_2SO_4$ and carefully removing the solvent under vacuum, the desired compound is obtained as a colourless oil (53.53 g; 242 mol), which needs no further purifications and is stored at −18° C.

Yield: 64%; TLC: Carrier: silica gel plate 60F 254 Merck; Eluent: $CHCl_3/CH_3OH/25\%$ $NH_4OH$ 90:9:1. Detection: 0.2% (w/v) ninhydrin in ethanol Rf=0.6; $^1$H-NMR, $^{13}$C-NMR, IR and MS spectra are consistent with the indicated structure.

B) N-[2-(1,1-Dimethylethoxy)-2-oxoethyl]-L-phenylalanine 1,1-Dimethyle-thyl Ester An emulsion of L-phenylalanine 1,1-dimethylethyl ester (compound prepared at point A) (53.53 g; 242 mol), tert-butyl bromoacetate (37.3 mL; 254 mol) in acetonitrile (400 mL) and 2M buffer phosphate pH 8 (200 mL) is vigorously stirred at room temperature for 16 hours. After separation, the organic phase is evaporated and the residue is taken up into EtOAc; the aqueous phase is extracted with EtOAc (3×200 mL). The combined organic phases are washed with water (2×300 mL), saline solution (200 mL) and finally dried over $Na_2SO_4$. The crude is purified by flash chromatography (n-hexane/EtOAc 9:1 to 75:25). After removing the solvents under vacuum, the desired compound is obtained as a colourless oil (66.04 g; 196.90 mol).

Yield: 81%; TLC: Carrier: silica gel plate 60F 254 Merck; Eluent: $CHCl_3/CH_3OH$ 95:5. Detection: 0.2% (w/v) ninhydrin in ethanol Rf=0.5; $^1$H-NMR, $^{13}$C-NMR, IR and MS spectra are consistent with the indicated structure.

C) Trifluoromethanesulfonic Acid 2-Bromoethyl Ester 240 g of trifluoromethanesulfonic anhydride (0.85 mol) are added in 1.5 h, under inert atmosphere, to a solution of bromoethanol (57 mL; 0.80 mol) and 2,6-lutidine (104 mL; 0.89 mol) in $CH_2Cl_2$ cooled at −5° C. After 10 min the mixture is concentrated to one fourth the volume, then eluted through a small layer of silica gel (eluent n-hexane/EtOAc= 9:1). By evaporation and drying, the desired product is obtained (147.2 g; 0.57 mol).

Yield: 72%; TLC: Carrier: silica gel plate 60F 254 Merck; Eluent: n-hexane/$iPr_2O$=8:2; Detection: 0.5% $KMnO_4$ in 1M NaOH Rf=0.6; $^1$H-NMR, $^{13}$C-NMR, IR and MS spectra are consistent with the indicated structure.

D) N-(2-Bromoethyl)-N-[2-(1,1-dimethylethoxy)-2-oxoethyl]-L-phenylalanine 1,1-Dimethyl Ester The intermediate prepared at point C) (147.2 g; 573 mol) is added under nitrogen to a solution of N-[2-(1,1-dimethylethoxy)-2-oxoethyl]-L-phenylalanine 1,1-dimethylethyl ester (65.93 g; 197 mol) and 2,6-lutidine (72 mL; 0.62 mol) in 600 mL of dry toluene at −15° C. After 16 h at room temperature, 200 mL of EtOAc, 200 mL of $H_2O$ and 50 mL of ethylenediamine are added to the mixture. The organic phase is washed with 300 mL of $H_2O$, 100 mL of acetate buffer pH=5.8, 100 mL of saturated aqueous $CuSO_4$ (hereinafter aq$CuSO_4$), 200 mL of saturated aq$NH_4Cl$, dried over $Na_2SO_4$ and evaporated. The residue is taken up into $iPr_2O$ and quickly filtered through a small layer of silica gel. By evaporation of the filtrate, the desired product is obtained (83.08 g; 188 mol).

Yield: 95.4%; GC assay: 97% (in % area); TLC: Carrier: silica gel plate 60F 254 Merck; Eluent: n-hexane/EtOAc= 9:1; Detection: 0.5% $KMnO_4$ in 1M NaOH Rf=0.5; $^1$H-NMR, $^{13}$C-NMR, IR and MS spectra are consistent with the indicated structure.

E) [(Phenylmethyl)amino]methylphosphonic Acid Diethyl Ester 1,3,5-Tribenzylhexahydro-1,3,5-triazine (98%; 12.48 g; 34.21 mol) is reacted with diethyl phosphite (94%; 15.5 mL; 113 mol) for 6 hours, under nitrogen atmosphere and at 100° C. The mixture is then cooled to room temperature, taken up with ethyl ether (150 mL) and acidified with 6N HCl (20 mL). The organic phase is extracted with 1N HCl (10 mL), the aqueous phases are basified with 5N KOH, then extracted with $Et_2O$ (300+150 mL), washed with brine (100 mL) and finally dried over $Na_2SO_4$. After evaporation of the solvent under vacuum, the product is recovered as a colourless oil (25.05 g; 97.37 mol) which is stored at a temperature of −18° C.

Yield: 95%; TLC: Carrier: silica gel plate 60F 254 Merck; Eluent: toluene/EtOAc/iPrOH 7:2:1; Detection: 254 nm; 0.5% $KMnO_4$ in 1M NaOH Rf=0.38; $^1$H-NMR, $^{13}$C-NMR, IR and MS spectra are consistent with the indicated structure.

F) Aminomethylphosphonic Acid Diethyl Ester

A solution of the compound prepared at point E (28.3 g; 110 mol) in methanol (600 mL) is stirred vigorously in the presence of $Pd(OH)_2/C$ (32 g) and $HCOONH_4$ (120 g) for 6 hours. The mixture is then filtered through a layer of Celite® and the filtered solution is evaporated to give a residue, which is taken up in ethanol (200 mL) and treated with Amberlite® IRA 400 resin in the OH⁻ form (150 mL, previously conditioned with absolute ethanol) for 3 hours. The suspension is then filtered and the solution is evaporated to dryness to obtain an oil (20.47 g) which is purified by flash chromatography ($CH_2Cl_2/CH_3OH/25\%$ $NH_4OH$ 954:40:6 to 89:10:1) to obtain 15.09 g (90.3 mol) of product as a colourless oil.

Yield: 82%; TLC: Carrier: silica gel plate 60F 254 Merck; Eluent: $CH_2Cl_2/CH_3OH/NH_4OH$ 25% 89:10:1; Detection: 254 nm; 0.5% $KMnO_4$ in 1M NaOH; 0.2% (w/v) ninhydrin in ethanol Rf=0.5; $^1$H-NMR, $^{13}$C-NMR, IR and MS spectra are consistent with the indicated structure.

G) N,N'-[[[(Diethoxyphosphinyl)methyl]imino]di-2,1-ethanediyl]bis[N-[2-(1,1-dimethylethoxy)-2-oxoethyl]-L-phenylalanine] 1,1-Dimethylethyl Ester An emulsion of the aminophosphonate prepared at point F) (8.29 g; 49.6 mol), bromide (prepared at point D) (62.92 g; 103.8 mol) in $CH_3CN$ (300 mL) and 2M phosphate buffer pH=8 (200 mL) is stirred vigorously at room temperature for 16 h. After replacing the aqueous phase with fresh buffer (200 mL) the mixture is stirred for a further 32 h. The organic phase is evaporated under reduced pressure, taken up with EtOAc, and the aqueous phase is repeatably extracted with EtOAc (3×150 mL). The combined organic phases are washed with $H_2O$, brine, dried over $Na_2SO_4$ and evaporated under reduced pressure. The crude product is purified by flash chromatography (eluent n-hexane/EtOAc/ iPrOH=7:3:0.1 to 6:4:0.2) to give the desired product. (31.38 g; 35.25 mol).

Yield: 71%; HPLC assay: 97% (in % area); TLC: Carrier: silica gel plate 60F 254 Merck; Eluent: n-hexane/$iPr_2O$= 65:35; Detection: 0.5% $KMnO_4$ in 1M NaOH Rf=0.6; $^1$H-NMR, $^{13}$C-NMR, IR and MS spectra are consistent with the indicated structure.

H) N,N'-[(Phosphonomethylimino)di-2,1-ethanediyl]bis[N-carboxymethyl-L-phenylalanine]

To a solution of the hexaester prepared at point G) (31.21 g; 35.06 mol) in 500 mL of $CH_3CN$ is slowly added, at −15° C., under inert atmosphere, iodotrimethylsilane (80 mL; 588 mol). The mixture is then stirred at room temperature for 3 days. After cooling on ice and adding $H_2O$ (300 mL), volatiles are removed under reduced pressure and the pH of the residual mixture is adjusted to 8 with 6N NaOH. The crude is then purified by chromatography through Amberlite® XAD 1600 resin eluting with water, 7% aq. $Na_2SO_3$ and finally with a $H_2O/CH_3CN$ gradient (95:5 30:70) to afford the desired product (19.66 g; 32.25 mol).

Yield: 92%;

HPLC assay: 100% (in % area);

Elemental analysis;

|  | C | H | N | P |  |
|---|---|---|---|---|---|
| % calc.: | 53.20 | 5.95 | 6.89 | 5.08 |  |
| % found: | 52.93 | 6.18 | 6.83 | 4.21 | $H_2O$ 1.51% |

TLC: Carrier: silica gel plate 60F 254 Merck
Eluent: n-hexane/EtOAc = 9:1
Detection: 0.5% $KMnO_4$ in 1M NaOH   Rf = 0.5
Specific rotation: $[\alpha]_{589}^{20}$ = +8.4; $[\alpha]_{578}^{20}$ = +8.7;
$[\alpha]_{546}^{20}$ = +10.6; $[\alpha]_{436}^{20}$ = +24.9;
$[\alpha]_{405}^{20}$ = +34.1; $[\alpha]_{365}^{20}$ = +55.1 (c 1.17; 0.5 N NaOH)

$^1$H-NMR, $^{13}$C-NMR, $^{31}$P-NMR, IR and MS spectra are consistent with the indicated structure.

I) Gadolinium Complex of N,N-[(Phosphonomethylimino) di-2,1-ethanediyl]bis[N-carboxymethyl-L-phenylalanine] Trisodium Salt To an aqueous solution of the compound prepared at point H (19.66 g, 32.25 mol) is added $GdCl_3 \cdot 6H_2O$ (32.25 mol) and 2N NaOH keeping pH within the range 6–7. The progress of the reaction is checked by HPLC. After 18 h the solution is filtered through a Millipore® filter, nanofiltered and concentrated (250 mL). The desalted solution is slowly percolated through a Dowex® $CCR_3LB$ column ($Na^+$ form; 35 mL) to obtain the desired product (25.48 g; 30.71 mol).

Yield: 95%; m.p.: >210° C. (dec.); HPLC assay: 100% (in % area); Elemental analysis:

|  | C | H | N | Gd | Na | P |
|---|---|---|---|---|---|---|
| % calc.: | 39.08 | 3.64 | 5.06 | 18.95 | 8.31 | 3.73 |
| % found: | 37.61 | 4.13 | 5.14 | 17.03 | 7.96 | 3.40 $H_2O$ 9.47% |

Specific rotation: $[\alpha]_{589}^{20}$ = −35.4; $[\alpha]_{578}^{20}$ = −36.8;
$[\alpha]_{546}^{20}$ = −42.5; $[\alpha]_{436}^{20}$ = −70.6;
$[\alpha]_{405}^{20}$ = −84.6; $[\alpha]_{365}^{20}$ = −110.0 (c 1.40; $H_2O$)

IR and MS spectra are consistent with the indicated structure.

EXAMPLE 2

Gadolinium Complex of [4S-(4R*,12R*)]-4-Carboxy-5,11-bis(carboxymethyl)-1-phenyl-12-[(phenylmethoxy)methyl]-8-(phosphono methyl)-2-oxa-5,8,11-triazatridecan-13-oic Acid, Salified with Na (1:3)

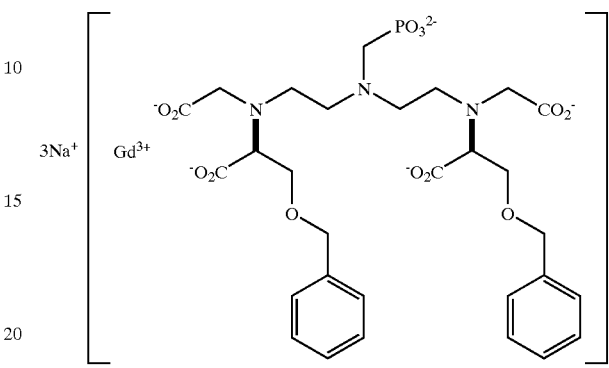

A) N-(2-Bromoethyl)-N-[2-(1,1-dimethylethoxy)-2-oxoethyl]-O-(phenylmethyl)-L-serine 1,1-Dimethylethyl Ester This intermediate is prepared analogously to that of Example 1, following the synthetic steps summarized in Scheme 1.

Alternatively, in a variation of the present process and in particular in this case, intermediate 4 is prepared as follows:

to a solution of N-[2-(1,1-dimethylethoxy)-2-oxoethyl]-N-(2-hydroxyethyl)-O-(phenylmethyl)-L-serine 1,1-dimethylethyl ester (prepared as described in WO 98/05625) (61.7 g; 150.7 mol) and triethylamine (31 mL; 0.22 mol) in dry THF (600 mL) are slowly added, under nitrogen atmosphere, methanesulfonyl chloride (12.5 mL; 160 mol) and lithium bromide (111 g; 1.25 mol) at −15/−10° C.

After evaporating the solvent and dissolving the residue in toluene and diethyl ether, the solution is washed with water and brine, then dried over $Na_2SO_4$ and evaporated to dryness, to obtain the title product as a colourless oil (69.79 g; 147.7 mol).

Yield: 98%; TLC: Carrier: silica gel plate 60F 254 Merck; Eluent: n-hexane/EtOAc=8:2; Detection: 0.5% $KMnO_4$ in 1M NaOH; $I_{2;\ 254}$ nm; Rf=0.75; $^1$H-NMR, $^{13}$C-NMR, IR and MS spectra are consistent with the indicated structure.

B) [4S-(4R*,12R*)]-8-[(Diethoxyphosphinyl)methyl]-4-[(1,1-dimethylethoxy)carbonyl]-5,11-bis[2-(1,1-dimethylethoxy)-2-oxoethyl]-1-phenyl-12-[(phenylmethoxy)methyl]-2-oxa-5,8,11-triazatridecan-13-oic Acid 1,1-Dimethylethyl Ester.

An emulsion of the aminophosphonate prepared as described in 1F (11.23 g; 67.20 mol) and the bromide, prepared as described in 2A, (68.72 g; 145.5 mol) in $CH_3CN$ (250 mL) and 2M phosphate buffer pH=8 (200 mL) is stirred vigorously at room temperature for 24 h. The phases are separated, the aqueous phase is repeatedly extracted with EtOAc (250+100 mL) and the organic phase is evaporated under reduced pressure, then taken up with EtOAc. The combined organic phases are washed with $H_2O$, brine and dried over $Na_2SO_4$. The crude is purified by flash chromatography (first column: eluent toluene/EtOAc/iPrOH= 80:18:2 to 66:31:3; second and third columns: eluent n-hexane/EtOAc/iPrOH 66:32:2). The solvent is evaporated under vacuum to obtain the product as a colourless oil (44.84 g; 47.19 mol).

Yield: 70%; TLC: Carrier: silica gel plate 60F 254 Merck; Eluent: n-hexane/EtOAc/iPrOH=50:45:5.; Detection: 0.5% KMnO$_4$ in 1M NaOH; I$_2$; 254 nm; Rf=0.5; $^1$H-NMR, $^{13}$C-NMR, IR and MS spectra are consistent with the indicated structure.

C) [4S-(4R*,12R*)]-4-Carboxy-5,11-bis(carboxymethyl)-1-phenyl-12-[(phenylmethoxy)methyl]-8-(phosphonomethyl)-2-oxa-5,8,11-triazatridecan-13-oic Acid To a solution of the hexaester prepared at point B (42.03 g; 44.23 mol) in 600 mL of CH$_3$CN is slowly added at −15° C., under inert atmosphere, iodotrimethylsilane (80 mL; 588 mol). The mixture is stirred at room temperature for 24 hours. After cooling on ice and adding water (150 mL), volatiles are removed under reduced pressure and pH is adjusted to 8 with 6N KOH. The resulting solution is concentrated, washed with Et$_2$O/EtOAc 1:1 (2×250 mL), CH$_2$Cl$_2$ (2×250 mL), heated to 50° C. and acidified to pH 2.6 with 6N HCl. After addition of CH$_3$CN (100 mL), the still hot resulting mixture is slowly loaded onto a column of Amberlite® XAD 1600 resin which is then eluted with water and subsequently with a H$_2$O,CH$_3$CN gradient (95:5 to 50:50), until complete elution of the product. The eluent mixture should be periodically heated to avoid precipitation of the product on to the column. After evaporation, the desired product is obtained as a white solid (23.52 g; 35.12 mol).

Yield: 79%; HPLC assay: 100% (in % area); Elemental analysis;

|  | C | H | N | P |  |
|---|---|---|---|---|---|
| % calc.: | 52.02 | 6.02 | 6.28 | 4.63 |  |
| % found: | 51.07 | 6.16 | 6.31 | 4.35 | H$_2$O 2.67% |
| Specific rotation: $[\alpha]_{589}^{20}$ = +14.5; $[\alpha]_{578}^{20}$ = +14.9; $[\alpha]_{546}^{20}$ = +17.0; $[\alpha]_{436}^{20}$ = +29.0; $[\alpha]_{405}^{20}$ = +35.4; $[\alpha]_{365}^{20}$ = +46.5 (c 1.06; CH$_3$OH) ||||||

$^1$H-NMR, $^{13}$C-NMR, $^{31}$P-NMR, IR and MS spectra are consistent with the indicated structure.

D) Gadolinium Complex of [4S-(4R*,12R*)]-4-Carboxy-5,11-bis(carboxymethyl)-1-phenyl-12-[(phenylmethoxy)methyl]-8-(phosphonomethyl)-2-oxa-5,8,11-triazatridecan-13-oic Acid, Salified with Na (1:3)

To a solution of the ligand prepared at point C (22.14 g; 33.06 mol) in a H$_2$O/CH$_3$CN 8:1 mixture (0.5 L) is added Gd$_2$O$_3$ (5.936 g; 16,37 mol) and 1N NaOH (80 mL). The reaction mixture is kept at 60° C. for 20 hours following the progress of the reaction by HPLC. The suspension is then filtered through a Millipore® filter, concentrated (120 mL) and percolated onto a Dowex® CCR$_3$LB column (Na$^+$ form; 50 mL). The eluate is first treated with Carbopuron® 2S, then filtered through paper and through Millipore® VC 0.1 filter μm. After evaporation the product is obtained as a white solid (30.51 g; 34.29 mol).

Yield: about 100%; m.p.:>250° C. (dec.); HPLC assay: 100% (in % area); Elemental analysis:

|  | C | H | N | Gd | Na | P |  |
|---|---|---|---|---|---|---|---|
| % calc.: | 39.15 | 3.85 | 4.72 | 17.67 | 7.75 | 3.48 |  |
| % found: | 35.62 | 4.46 | 4.43 | 16.00 | 6.86 | 2.86 | H$_2$O 8.54% |
| Specific rotation: $[\alpha]_{589}^{20}$ = −26.0; $[\alpha]_{578}^{20}$ = −27.4; $[\alpha]_{546}^{20}$ = −31.2; $[\alpha]_{436}^{20}$ = −50.0; $[\alpha]_{405}^{20}$ = −58.3; $[\alpha]_{365}^{20}$ = −72.1 (c 1.115; H$_2$O) ||||||||

IR and MS spectra are consistent with the indicated structure.

EXAMPLE 3

Gadolinium Complex of N,N'-[(Phosphonomethylimino)di-2,1-ethanediyl]bis[N-carboxymethyl-L-tryptophan], Salified with Na (1:3)

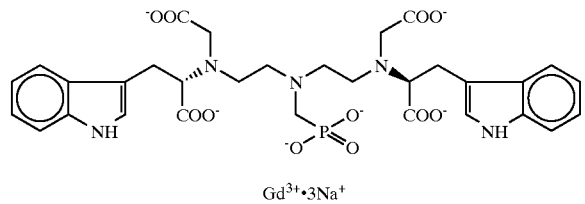

Gd$^{3+}$·3Na$^+$

A) N-[(Phenylmethoxy)carbonyl]-L-tryptophan 1,1-Dimethylethyl Ester

To a suspension of N-[(phenylmethoxy)carbonyl]-L-tryptophan (33.27 g; 98.32 mol) (previously prepared by reacting L-tryptophan with CBZCl, in H$_2$O and 1N NaOH), benzyltriethylammonium chloride (BTEAC) (22.4 g; 98.32 mol) and K$_2$CO$_3$ (176.91 g; 1.28 mol) in dimethylacetamide (750 mL) is added tert-butyl bromide (265 mL; 2.36 mol). The solution is heated to 55° C. and vigorously stirred for 19 hours. The mixture is then cooled to room temperature, diluted with H$_2$O (3L) and then extracted with EtOAc (2×1L). The organic phases are evaporated to dryness to obtain the title product as a pale yellow oil (36 g; 98 mol)

Yield: 99%; HPLC assay: 99% (in % area); TLC: Carrier: silica gel plate 60F 254 Merck; Eluent: n-hexane/EtOAc= 7:3; Detection: 0.5% KMnO$_4$ in 1M NaOH; 254 nm; Rf=0.44; $^1$H-NMR, $^{13}$C-NMR, IR and MS spectra are consistent with the indicated structure.

B) N-[2-(1,1-Dimethylethoxy)-2-oxoethyl]-L-tryptophan 1,1-Dimethylethyl Ester

To a solution of L-tryptophan 1,1-dimethylethyl ester (17.10 g; 65.68 mol), obtained by catalytic hydrogenation of the product prepared at point A, in CH$_3$CN (150 mL) and 2M buffer phosphate (pH 8; 150 mL) is added tert-butyl bromoacetate (10.7 mL; 72.25 mol) and the resulting mixture is left for 23 hours under strong stirring. The organic phase is separated and concentrated to a residue which is purified by flash chromatography (eluent n-hexane/EtOAc, 8:2) to afford the desired product as pale red oil (20.07 g; 53.59 mol).

Overall yield: 54.5% (from L-tryptophan); HPLC assay: 100% (in % area); TLC: Carrier: silica gel plate 60F 254 Merck; Eluent: n-hexane/EtOAc=7:3; Detection: 0.5% KMnO$_4$ in 1M NaOH; 254 nm; Rf=0.28; $^1$H-NMR, $^{13}$C-NMR, IR and MS spectra are consistent with the indicated structure.

C) N-[2-(1,1-Dimethylethoxy)-2-oxoethyl]-N-(2-hydroxyethyl)-L-tryptophan 1,1-Dimethylethyl Ester A jacketed reactor is loaded with a solution of N-[2-(1, 1-dimethylethoxy)-2-oxoethyl]-L-tryptophan 1,1-dimethylethyl ester (5 g; 13.35 mol) prepared at point B, in CH$_3$CN (25 mL). To the solution cooled to −80° C. is added ethylene oxide (13 mL; 0.26 mol) and ytterbium triflate (0.83 g; 1.34 mol). The mixture is then slowly warmed to room temperature then, after 15 hours, diluted with water (50 mL) and extracted with Et$_2$O (3×50 mL). The organic phases are evaporated to dryness to obtain a crude which is purified by flash chromatography (eluent n-hexane/EtOAc 7:3) to give the desired product as a pale yellow oil (4.32 g; 10.32 mol).

Yield: 77%; HPLC assay: 99% (in % area); TLC: Carrier: silica gel plate 60F 254 Merck; Eluent: n-hexane/EtOAc= 7:3; Detection: 0.5% $KMnO_4$ in 1M NaOH; 254 nm; Rf=0.23; $^1$H-NMR, $^{13}$C-NMR, IR and MS spectra are consistent with the indicated structure.

D) N-(2-Bromoethyl)-N-[2-(1,1-dimethylethoxy)-2-oxoethyl]-L-tryptophan 1,1-Dimethylethyl Ester To a solution of intermediate C (4.64 g; 11.09 mol) in $CH_2Cl_2$ (44 mL) is added, under nitrogen, $Ph_3P$ (2.9 g; 11.09 mol). To the resulting mixture cooled to 0° C. is added NBS (1.97 g; 11.09 mol) in portions. After 3 hours at 0° C. and 1 hour at room temperature, the solution is concentrated until $Ph_3PO$ precipitates as a white solid. The mixture is then kept at 4° C. for 72 hours to complete precipitation. The precipitate is filtered and the filtrate is concentrated to give a crude which is purified by flash chromatography (eluent n-hexane/EtOAc 8:2) to afford the desired product as a pale yellow oil (4.46 g; 9.26 mol).

Yield: 83%; HPLC assay: 94% (in % area); TLC: Carrier: silica gel plate 60F 254 Merck; Eluent: n-hexane/EtOAc= 8:2; Detection: 0.5% $KMnO_4$ in 1M NaOH; 254 nm; Rf=0.42; $^1$H-NMR, $^{13}$C-NMR, IR and MS spectra are consistent with the indicated structure.

E) N,N'-[[[(Diethoxyphosphinyl)methyl]imino]di-2,1-ethanediyl]bis(N-[2-(1,1-dimethylethoxy)-2-oxoethyl]-L-tryptophan 1,1-Dimethylethyl Ester]

To a solution of aminomethylphosphonic acid diethyl ester (prepared as in example 1F) (5.25 g; 31.41 mol) and of the intermediate prepared at point 3D (30.25 g; 62.82 mol) in $CH_3CN$ (100 mL) is added 2M phosphate buffer pH 8 (200 mL). The resulting biphasic mixture is kept under strong stirring for 18 hours; the organic layer is then separated and concentrated to obtain a crude oil which is purified by flash chromatography (eluent n-hexane/EtOAc/$CH_3OH$ 9:1:0.5) to give the hexaester as a waxy solid (21.6 g; 22.3 mol).

Yield: 71%; HPLC assay: 100% (in % area); TLC: Carrier: silica gel plate 60F 254 Merck; Eluent: n-hexane/EtOAc/$CH_3OH$ 9:1:0.5; Detection: 0.5% $KMnO_4$ in 1M NaOH; 254 nm; Rf=0.40; $^1$H-NMR, $^{13}$C-NMR, IR and MS spectra are consistent with the indicated structure.

F) N,N'-[(Phosphonomethylimino)di-2,1-ethanediyl]bis[N-carboxymethyl-L-tryptophan]

To a solution of the hexaester (15.17 g; 15.67 mol) prepared as in point E, in $CH_3CN$, (200 mL) is added, under nitrogen atmosphere and at 0° C., $(CH_3)_3SiI$ (32 mL; 0.235 mol). The solution is then stirred at room temperature for 22 hours. After cooling to –5° C., the mixture is diluted with $H_2O$ (30 mL) and washed with $Et_2O$ (2×400 mL). The aqueous layer is separated, neutralized to pH 7 with 2N NaOH and concentrated to 80 mL. After cooling to 0–5° C., the mixture is acidified by addition of 2N HCl (32 mL) to obtain a precipitate which is filtered, washed with $H_2O$ and dried to obtain the desired product as a crystalline white solid (8.37 g; 12.17 mol).

Yield: 78%; m.p.: 157–160° C.; HPLC assay 98% (in % area); Elemental analysis;

|  | C | H | N | P |  |
| --- | --- | --- | --- | --- | --- |
| % calc.: | 54.15 | 5.57 | 10.18 | 4.50 |  |
| % found: | 50.13 | 5.80 | 9.34 | 4.35 | $H_2O$ 7.78% |

Specific rotation: $[\alpha]_{589}^{20} = -10.69$; $[\alpha]_{578}^{20} = -11.19$; $[\alpha]_{546}^{20} = -12.38$; $[\alpha]_{436}^{20} = -16.54$; (c 2.02; NaOH 0.1N)

$^1$H-NMR, $^{13}$C-NMR, $^{31}$P-NMR, IR and MS spectra are consistent with the indicated structure.

G) Gadolinium Complex of N,N'-[(Phosphonomethylimino)di-2,1-ethanediyl]bis[N-carboxymethyl-L-tryptophan] Trisodium Salt To a suspension of chelating agent (6.0 g; 8.72 mol) prepared as in point F in $H_2O$ (80 mL) cooled to 5° C. is added at first 1N NaOH (28 mL) to obtain a clear solution, and then $GdCl_3$ (0.17M solution) (51 mL; 8.72 mol) keeping pH at 7 by simultaneous addition of 1N NaOH. The solution is left at room temperature for 1 hour, filtered through Millipore® HAWP 0.45 filter μm and subsequently percolated through an Amberlite® XAD 1600 column eluting with $H_2O$. The eluate is evaporated to dryness to obtain the product as a white solid (7.12 g; 7.85 mol).

Yield: 90%; m.p.:>250° C. (dec.); HPLC assay: 99.6% (in % area); Elemental analysis:

|  | C | H | N | Gd | Na | P |  |
| --- | --- | --- | --- | --- | --- | --- | --- |
| % calc.: | 41.02 | 3.55 | 7.71 | 17.32 | 7.60 | 3.41 |  |
| % found: | 36.18 | 4.42 | 7.55 | 16.79 | 6.54 | 3.18 | $H_2O$ 11.74% |

Specific rotation: $[\alpha]_{589}^{20} = -20.96$; $[\alpha]_{578}^{20} = -21.60$; $[\alpha]_{546}^{20} = -24.55$; $[\alpha]_{436}^{20} = -40.61$; $[\alpha]_{405}^{20} = -47.83$; $[\alpha]_{365}^{20} = -60.85$ (c 2.505; $H_2O$)

IR and MS spectra are consistent with the indicated structure.

EXAMPLE 4

Gadolinium Complex of N,N-bis[2-[(Carboxymethyl)(phosphonomethyl)amino]ethyl]-O-(4-hydroxyphenyl)-3,5-diiodo-L-tyrosine Salified with Sodium (1:5)

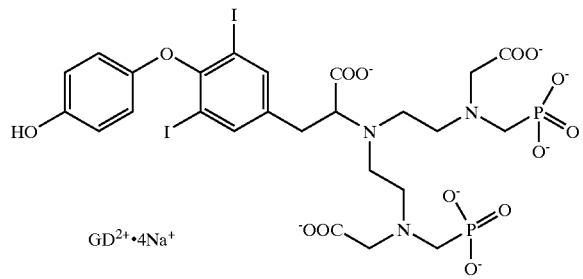

A) [[(2-Hydroxyethyl)(phenylmethyl)amino]methyl]phosphonic Acid 1,1-Dimethylethyl Ester To a solution of 2-benzylaminoethanol (30.59 g; 196 mol) in water (30 mL), cooled on an ice bath, is added formaldehyde (35% aqueous solution, 16.3 mL; 205 mol). After 5 minutes the mixture is warmed to room temperature then extracted with $CHCl_3$ (3×40 mL). The organic phases are dried over $MgSO_4$, evaporated to dryness recovering the aminal (intermediate 2 of Scheme 2) as a colourless oil which is further dried over $P_2O_5$, under vacuum.

To a solution of di-tert-butyl phosphite (38.12 g; 196 mol) and triethylamine (28.0 mL; 200 mol) in $CH_2Cl_2$ (300 mL) is slowly added (in 30 min) chlorotrimethylsilane (26.5 mL; 197 mol) and stirred for 10 min. To the resulting mixture, containing the intermediate, is then added a solution of the above prepared aminal in $CH_2Cl_2$ (100 mL), then ytterbium triflate (12.36 g; 19.9 mol) and the reaction is kept at room temperature for 1.5 hours. After addition of water and further $CH_2Cl_2$, insoluble salts are filtered through Celite® and the solution is concentrated under vacuum. The resulting intermediate is not isolated, but is diluted with an AcOH/

THF/$H_2O$ mixture 3:1:1 (250 mL) and the resulting homogeneous solution is concentrated under vacuum; most AcOH is removed by azeotropic distillation with toluene and $H_2O$ and the pH of the solution is adjusted to neutrality by addition of $Na_2CO_3$. The mixture is extracted with EtOAc (3×80 mL), the organic phase is dried over $MgSO_4$ and then evaporated to dryness to obtain the product as a colourless oil (43.46 g; 122 mol).

Yield: 62%; TLC: Carrier: silica gel plate 60F 254 Merck; Eluent: $iPr_2O/CH_2Cl_2/iPrOH$=70:25:5; Detection: 0.5% $KMnO_4$ in 1M NaOH; 254 nm; $I_2$; Rf=0.38; $^1$H-NMR, $^{13}$C-NMR, IR and MS spectra are consistent with the indicated structure.

B) [[(2-Hydroxyethyl)amino]methyl]phosphonic Acid 1,1-Dimethylethyl Ester

To a solution of intermediate A (43.46 g; 122 mol) in dry MeOH (1 L) is carefully added, under nitrogen, $Pd(OH)_2/C$ (40 g) as a catalyst. The mixture is then vigorously stirred in an $H_2$ atmosphere and for 2 h. After filtration through $MgSO_4$ and Celite ° the resulting solution is evaporated. Residual methanol is evaporated by azeotropic distillation with cyclohexane to obtain the desired intermediate as a colourless oil (39.45 g) which, although containing traces of solvents, can be used (as it is) in the subsequent reaction without further purification.

TLC: Carrier: silica gel plate 60F 254 Merck; Eluent: $CH_2Cl_2/CH_3OH/25\%$ (w/w) $NH_4OH$ 89:10:1; Detection: 0.5% $KMnO_4$ in 1M NaOH; 2% ninhydrin in ethanol; Rf=0.5; $^1$H-NMR, $^{13}$C-NMR, IR and MS spectra are consistent with the indicated structure.

C) N-[[Bis(1,1-dimethylethoxy)]phosphonomethyl]-N-(2-hydroxyethyl)-glycine 1,1-Dimethylethyl Ester An emulsion of intermediate B as it is isolated (39.45 g), tert-butyl bromoacetate (17.8 mL; 121 mol) in acetonitrile (250 mL) and 2M buffer phosphate pH 8 (200 mL) is vigorously stirred at room temperature for 4 days. The phases are separated; the organic phase is evaporated and the residue is treated with EtOAc (3×150 mL). The combined organic phases are washed with $H_2O$ (2×200 mL), brine (100 mL) and dried over $Na_2SO_4$. The crude is purified by flash chromatography eluting at first with $iPr_2O/CH_2Cl_2/iPrOH$=70:30:2, then with $Et_2O/CH_2Cl_2/iPrOH$ 70:30:2 to 60:40:3 to afford the desired intermediate as a colourless oil (28.71 g; 75.27 mol)

Yield: 62%; TLC: Carrier: silica gel plate 60F 254 Merck; Eluent: $iPr_2O/CH_2Cl_2/iPrOH$=60:35:5; Detection: 0.5% $KMnO_4$ in 1M NaOH; $I_2$; Rf=0.4; $^1$H-NMR, $^{13}$C-NMR, IR and MS spectra are consistent with the indicated structure.

D) N-[[bis(1,1-Dimethylethoxy)]phosphonomethyl]-N-(2-bromoethyl)glycine 1,1-Dimethylethyl Ester To a solution of intermediate C and triethylamine in dry THF (500 mL) cooled at −15° C., is slowly added, under nitrogen, methanesulfonyl chloride (2.8 mL; 36.1 mol). After 1.5 hours at −10° C. lithium bromide (25.0 g; 288 mol) is added and the mixture is left under strong stirring for 16 hours while gradually warming to room temperature. Most volatiles are then evaporated off under reduced pressure; the residue is diluted with EtOAc (300 mL) and $Et_2O$ (300 mL) and washed with $H_2O$ (2×200 mL). The organic phase is washed with $H_2O$/brine 1:1 (200 mL), brine (100 mL) and finally dried over $Na_2SO_4$. After evaporation of the solvents the crude residue is purified by flash chromatography (eluent n-hexane/$Et_2O$/iPrOH 1:1:0.01) to afford the desired intermediate (12.35 g; 27.79 mol) which crystallizes on storing at −18° C.

Yield: 83%; m.p.: 50–51° C.; TLC: Carrier: silica gel plate 60F 254 Merck; Eluent: $iPr_2O$/EtOAc=8:2; Detection: 0.5% $KMnO_4$ in 1M NaOH; $I_2$; Rf=0.35; $^1$H-NMR, $^{13}$C-NMR, IR and MS spectra are consistent with the indicated structure.

E) N,N-bis[2-[[2-(1,1-Dimethylethoxy)-2-oxoethyl][[(1,1-dimethylethoxy)phosphinyl]methyl]amino]ethyl]-O-(4-hydroxyphenyl)-3,5-diiodo-L-tyrosine 1,1-Dimethylethyl Ester An emulsion of intermediate D (12.05 g; 27.12 mol) and 3,5-diiodo tyrosine methyl ester (5.85 g; 10.85 mol) in acetonitrile and 2M phosphate buffer pH 8 is vigorously stirred at room temperature for 72 hours. The aqueous phase is replaced with fresh buffer and the solution is left under stirring for a further three days. The phases are then separated; the aqueous layer is extracted with EtOAc (250+100 mL), the organic layer is evaporated and the residue is taken up into EtOAc. The combined EtOAc solutions are washed with $H_2O$ (100 mL), $H_2O$brine 1:1 (100 mL), brine (100 mL). After drying over $Na_2SO_4$ and evaporation of the solvent the residue is purified by flash chromatography (eluent n-hexane/$Et_2O$/iPrOH 72:20:8). The desired intermediate is obtained (intermediate 8, according to scheme 2) as a colourless oil (11.32 g; 8.94 mol).

Yield: 82%; HPLC assay: 98.2% (in % area); TLC: Carrier: silica gel plate 60F 254 Merck; Eluent: toluene/EtOAc/iPrOH 1:1:0.02; Detection: 0.5% $KMnO_4$ in 1M NaOH; 254 nm; 12; Rf=0.40; $^1$H-NMR, $^{13}$C-NMR, IR and MS spectra are consistent with the indicated structure.

F) N,N-bis[2-[(Carboxymethyl)(phosphonomethyl)amino]ethyl]-O-(4-hydroxyphenyl)-3,5-diiodo-L-tyrosine To a solution of polyester E) (24.9 g; 19.6 mol) in 1,4-dioxane (100 mL) is added 4N HCl (180 mL). The solution is heated to 70° C. for 3 hours then at 90° C. for 1 hour, following the progress of the reaction by HPLC. The mixture is cooled to room temperature, concentrated to 200 mL and slowly loaded onto an Amberlite® XAD 1600 column. After a first elution with $H_2O$, an elution gradient based on $H_2O/CH_3CN$ is used to afford the desired product as a white solid (15.5 g; 16.86 mol).

Yield: 86%; HPLC assay: 100% (in % area); Elemental analysis;

|  | C | H | N | I | P |
|---|---|---|---|---|---|
| % calc.: | 32.81 | 3.63 | 4.59 | 27.23 | 6.77 |
| % found: | 31.11 | 3.78 | 4.33 | 26.11 | 6.57 $H_2O$ 3.96% |

Specific rotation: $[\alpha]_{589}^{20}$ = +7.5; $[\alpha]_{578}^{20}$ = +7.8; $[\alpha]_{546}^{20}$ = +9.2; $[\alpha]_{436}^{20}$ = +18.1; $[\alpha]_{405}^{20}$ = +23.1; $[\alpha]_{365}^{20}$ = +33.3
(c 1.03; $CH_3COOH$/HCl 6N 4:1)

$^1$H-NMR, $^{13}$C-NMR, IR and MS spectra are consistent with the indicated structure.

G) Gadolinium Complex of N,N-Bis[2-[(Carboxymethyl)(phosphonomethyl)amino]ethyl]-O-(4-hydroxyphenyl)-3,5-diiodo-L-tyrosine Salified with Sodium (1:5)

To an aqueous solution of ligand F) (15.33 mol) at pH 7 is added $Gd_2O_3$ (2.80 g; 15.39 mol). The solution is diluted to 2 L with $H_2O$ and heated at 70° C. for 6 hours following the progress of the complexation by HPLC. Since the conversion is only about 14.5%, the solution is added, under stirring, with a solution of 0.164 M $aqGdCl_3$ (78.0 mL; 12.8 mol), keeping pH at about 7 with 2N NaOH. After completion of the complexation the mixture is filtered through a Millipore® HAWP 0.45 μm filter, concentrated to 1 L and percolated through a Dowex® $CCR_3LB$ column, $Na^+$ form. The eluate is concentrated to 250 mL and nanofiltered. After concentration under vacuum, the dark solution obtained is treated with Carbopuron® 2S at 60° C., filtered and finally freeze-dried to obtain a solid which still contains chloride ions, which is then dissolved in H₂O and purified by elution over Amberlite® XAD 1600, eluting at first with H₂O, then with a H₂O/CH₃CN gradient to afford the desired Gd complex (12.67 g; 10.74).

The purification of the complex on weakly cation-exchange resin yielded the product with the phenol group deprotonated, as confirmed by the elemental analysis.

Yield: 70%; m.p.: >280° C.; HPLC assay: 99.5% (in % area); Elemental analysis;

|  | C | H | Gd | I | N | Na | P |  |
|---|---|---|---|---|---|---|---|---|
| % calc.: | 25.46 | 2.14 | 13.33 | 21.52 | 3.56 | 9.75 | 5.25 |  |
| % found: | 24.01 | 3.09 | 12.44 | 20.19 | 3.35 | 8.52 | 5.16 | H₂O 6.56% |

IR and MS spectra are consistent with the indicated structure.

EXAMPLE 5

Gadolinium Complex of N,N'-[(Phosphonomethylimino)di-2,1-ethanediyl]bis[N-(carboxymethyl)glycine] Salified with Na (1:3)

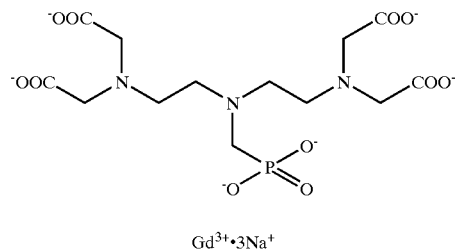

Gd³⁺·3Na⁺

A) N,N'-[[[(Diethoxyphosphinyl)methyl]imino]di-2,1-ethanediyl]bis[N-[2-(1,1-dimethylethoxy)-2-oxoethyl]glycine] 1,1-Dimethylethyl Ester The product is prepared by reacting the aminophosphonate (15.09 g; 90.28 mol) prepared as described in 1F and the bromide (70.09 g; 199.0 mol) prepared as described in J. Org. Chem. 1993, 58, 1151. The reaction is carried out as reported in 1G and the product is recovered as a colourless oil (35.59 g; 50.14 mol).

Yield: 56%; HPLC assay: 95% (in % area); TLC. Carrier: silica gel plate 60F 254 Merck; Eluent: toluene/EtOAc/iPrOH=50:45:5; Detection: 0.5% KMnO₄ in 1M NaOH; 254 nm; Rf=0.40; ¹H-NMR, ¹³C-NMR, IR and MS spectra are consistent with the indicated structure.

B) N,N'-[(Phosphonomethylimino)di-2,1-ethanediyl]bis[N-(carboxymethyl)-glycine]

The hexaester prepared at point A (29.23 g; 41.18 mol) is deprotected with iodomethylsilane, under the same conditions as reported in 1H. The resulting crude is loaded onto a Relite® 3 AS/fb column which is eluted with water until elimination of the residual iodide and then onto a column of Dowex® CCR₃LB resin maintained at 60° C. The solution comprising the purified compound is freeze-dried to obtain the chelating agent as a white solid (9.69 g; 22.6 mol).

Yield: 55%; m.p.: 110–114° C.; HPLC assay: 96% (in % area); Elemental analysis;

|  | C | H | N | P |  |
|---|---|---|---|---|---|
| % calc.: | 36.37 | 5.63 | 9.79 | 7.21 |  |
| % found: | 35.03 | 5.76 | 9.43 | 6.92 | H₂O 1.05% |

¹H-NMR, ¹³C-NMR, IR and MS spectra are consistent with the indicated structure.

C) Gadolinium Complex of N,N'-[(Phosphonomethylimino)di-2,1-ethanediyl]bis[N-(carboxymethyl)glycine]Trisodium Salt.

To a solution of the chelating agent obtained as in step B (6.0 g; 13.97 mol) in H₂O (60 mL) is added 2N NaOH (15 mL) and Gd₂O₃ (2.53 g; 6.99 mol). The suspension is heated at 70° C. for one hour, then filtered through Millipore® HAWP 0.45 μm filter. The solution is neutralized with 2N NaOH and concentrated to dryness to obtain the title complex as a white solid (9.1 g; 14 mol) in quantitative yield.

m.p.:>250° C.; HPLC assay: 100% (in % area); Elemental analysis;

|  | C | H | Gd | N | Na | P |
|---|---|---|---|---|---|---|
| % calc.: | 24.04 | 2.79 | 24.21 | 6.47 | 10.62 | 4.77 |
| % found.: | 23.94 | 3.00 | 24.06 | 6.45 | 10.74 | 4.71 |

IR and MS spectra are consistent with the indicated structure.

EXAMPLE 6

Gadolinium Complex of N,N'-[(Phosphonomethylimino)di-2,1-ethanediyl]bis[N-(phosphonomethyl)glycine] Salified with Na (1:5)

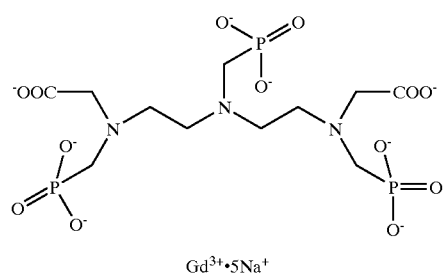

Gd³⁺·5Na⁺

The aminomethylphosphonic acid diethyl ester, prepared as described in example 1F, is reacted with the bromo derivative prepared according to Example 4D.

The resulting hexaester is deprotected under the same conditions as reported in 4F. The isolated acidic chelating agent is complexed according to the procedure reported in 3G.

EXAMPLE 7

Gadolinium Complex of N,N'-[[[3-Carboxy-1-phosphonopropyl]imino]di-2,1-ethanediyl]bis[-(carboxymethyl)glycine] Salified with Triethylamine (1:4)

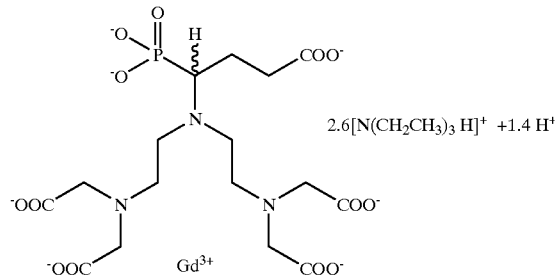

A) 2,2'-(Iminodi-2,1-ethanediyl)bis-1H-isoindole-1,3(2H)-dione)

A mixture of phthalic anhydride (32.0 g; 0.216 mol) and diethylenetriamine (10.32 g; 0.1 mol) in acetic acid (106 g) is refluxed for 1 h. The acetic acid is removed on a rotary evaporator and the pale yellow oil obtained is allowed to stand under vacuum overnight. The oil solidified on standing and this is then triturated with a saturated solution of sodium bicarbonate to remove acetic acid and some unreacted phthalic anhydride. The yellow solid is then filtered, washed with water, dissolved with chloroform (500 mL), and the chloroform solution is dried with $Na_2SO_4$. Evaporation of the chloroform gave a solid (28.0 g).

Yield: 77.1%.

An analytical sample is crystallized from ethanol.

mp: 180–81° C.; $^1$H-NMR, $^{13}$C-NMR, IR and MS spectra are consistent with the indicated structure. HPLC assay: 96.7% (in % area).

B) 4-[bis[2-(1,3-Dihydro-1,3-dioxo-2H-isoindol-2-yl)ethyl]amino]-4bis[1,1-dimethylethoxy)phosphinyl]butanoic Acid Phenylmethyl Ester A solution of the 3-benzyloxycarbonylpropionaldehyde (4.0 g; 0.0208 mol) in acetonitrile (25 mL) is added to a slurry of bis(phthalimido) derivative prepared at point A) (6.8 g; 0.0187 mol) in acetonitrile (75 mL) over a period of 30 min. The temperature of the reaction mixture is maintained at 80–90° C. during the addition. The reaction mixture is stirred at 80° C. for an additional 30 min. The colour of the reaction mixture turns yellow during the addition of the aldehyde. Tris(tert-butyl) phosphite (5.2 g; 0.0208 mol) in acetonitrile (15 mL) is added dropwise and the reaction mixture is stirred at room temperature for 48 h. The reaction mixture becomes a clear yellow solution after the addition of tris(tert-butyl)phosphite (~3 h). Acetonitrile is then removed and the residue is treated with EtOAc (50 mL). The solid formed is filtered and the EtOAc solution is directly applied to a column of silica gel (packed in 50:50 hexane-EtOAc). The column is initially eluted with hexane-EtOAc (600 mL) and then eluted with 70:30 (EtOAc:hexane). Fractions containing the product are collected and evaporated to give an oil. This is dried under vacuum to give a white solid (9.9 g).

Yield 72%.

An analytical sample is crystallised from hexane-EtOAc.

mp.: 120–121° C.; HPLC assay: 99.2% (in % area); Elemental analysys;

|  | C | H | N |
|---|---|---|---|
| % calc.: | 64.00 | 6.30 | 5.70 |
| % found: | 63.90 | 6.34 | 5.54 |

$^1$H-NMR, $^{13}$C-NMR, IR and MS spectra are consistent with the indicated structure.

C) 4-[bis(2-Aminoethyl)amino]-4-[bis(1,1-dimethylethoxy)phosphinyl]butanoic Acid Phenylmethyl Ester To a solution of tert-butoxyphosphinyl derivative prepared at point B) (5.65 g; 0.0078 mol) in $CH_2Cl_2$ (50.0 mL) is added hydrazine (1.5 g; 0.0468 mol) followed by water (0.2 mL) and the reaction mixture is stirred at room temperature. The reaction is followed by $^1$H NMR (the reaction is complete in 36 h). The precipitated phthalyl hydrazide is filtered through Celite® and the filter cake is washed with $CH_2Cl_2$. The combined methylene chloride solution is evaporated to give a thick oil, which is dried under vacuum. The diamine obtained (3.61 g) is used for the alkylation step without further purification.

Yield: 97%. $^1$H-NMR, $^{13}$C-NMR, IR and MS spectra are consistent with the indicated structure.

D) N,N'-[[[-[bis(1,1-Dimethylethoxy)phosphinyl-3-[(phenylmethoxy)carbonyl]propyl]imino]di-2,1-ethanediyl]bis[N-(2-(1,1-dimethylethoxy)-2-oxoethyl]glycine 1,1-Dimethylethyl Ester]

To a solution of the diamino intermediate prepared at point C) (7.5 g; 0.0159 mol) in acetonitrile (60 mL) are added diisopropylethylamine (18.55 g; 25 mL; 0.142 mol) and tert-butyl bromoacetate(13.2 g; 10.0 mL; 0.0695 mol) and the mixture is stirred at room temperature overnight. Acetonitrile and excess diisopropylethylamine are removed on a rotary evaporator and the residue is basified with $K_2CO_3$ solution (5%, 100 mL). The reaction mixture is extracted with diethylether (2×150 mL) and the diethylether solution is washed with water and dried ($Na_2SO_4$). Evaporation of diethylether gives an oil, which is purified by silica gel chromatography. The column is packed with hexane-EtOAc (7:3) and eluted with hexane-EtOAc (7:3) (500 mL) and then with hexane-EtOAc (5:5). Fractions (Rf 0.5) comprising the desired compound are collected and evaporated to give a thick viscous oil (7.5 g).

Yield: 51%. $^1$H-NMR, $^{13}$C-NMR, IR and MS spectra are consistent with the indicated structure.

E) N,N'-[[[1-[(bis(1,1-dimethylethoxy)phosphinyl]-3-carboxypropyl]imino]di-2,1-ethanediyl]bis[N-[2-(1,1-dimethylethoxy)-2-oxoethyl]glycine 1,1-Dimethylethyl Ester]

To a solution of the benzylester prepared at point D) (4.63 g; 0.005 mol) in THF (30 mL) is added 10% Pd-C (2.0 g, Degussa type ~50% water) and the mixture is hydrogenated at 45 psi for 12 h. The catalyst is filtered through Celite® and the filter cake is washed with THF (2×30 mL). The combined THF solution is concentrated on a rotary evaporator to give the acid as a thick viscous oil. This is dried under vacuum for 24 h isolating the desired compounds (3.98 g) which is used as such without further purification.

Yield: 95.2%; $^1$H-NMR, $^{13}$C-NMR, IR and MS spectra are consistent with the indicated structure.

F) N,N'-[[[3-Carboxy-1-phosphonopropyl]imino]di-2,1-ethanediyl]bis[N-(carboxymethyl)glycine]

The hexaester prepared at step B) (0.84 g, 0.001 mol) is dissolved in TFA and the mixture is stirred at room temperature for 24 h. TFA is removed on a rotary evaporator and the residue is treated with anhydrous diethylether (10 mL).

The precipitated solid is filtered and dried under vacuum to give the acid chelating ligand as TFA salt (0.45 g).

Yield: 90%; HPLC assay: 86% (in % area); $^1$H-NMR, $^{13}$C-NMR, IR and MS spectra are consistent with the indicated structure.

G) Gadolinium Complex of N,N'-[[[3-Carboxy-1-phosphonopropyl]imino]di-2,1-ethanediyl]bis[N-(carboxymethyl)glycine] Salified with Triethylamine The acid chelating ligand TFA salt obtained at step F) (0.25 g) is dissolved in a mixture of acetonitrile water 1:1 (5 mL) and Gd (OAc)$_3$ (0.25 g; 0.006 mol) is then added to the reaction mixture. The initial pH of the reaction mixture is found to be 1.29. The pH of the solution is then adjusted to 5.0 by the addition of 1N NaOH and the mixture is stirred at room temperature for 24 h. The Gd complex is then purified by DEAE Sephadex chromatography using triethylamine bicarbonate buffer. The fractions eluted at 800-mM buffer are collected and freeze dried to give the Gd complex as a triethylamine salt (0.2 g).

PLC assay: 100% (in % area); Elemental Analysis: Calcd. for $C_{16}H_{25}N_3O_{13}PGd \cdot 2.6C_6H_{15}N \cdot 3.H_2O$;

|  | C | H | Gd | N | H$_2$O |
|---|---|---|---|---|---|
| % calc.: | 39.02 | 7.25 | 16.10 | 8.06 | 3.00 |
| % found.: | 39.09 | 7.33 | 16.19 | 8.25 | 3.03 |

IR and MS spectra are consistent with the indicated structure.

EXAMPLE 8

Gadolinium Complex of 4-Phenyl-N-[trans-4-[[[4-[bis[2-bis(carboxymethyl)amino]ethyl]amino]-1-oxo-4-phosphonobutyl]amino]methyl]cyclohexylcarbonyl]-L-phenylalanine, Salified with Meglumine (1:4)

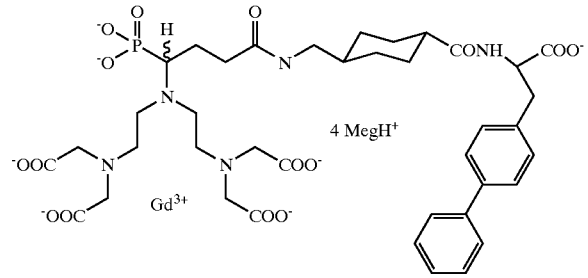

A) 4-Phenyl-N[[[trans-4-[bis[2-[bis2(1,1-dimethylethoxy)-2-oxoethyl]amino]ethyl]amino]-4-bis[1,1-dimethylethoxy)phosphinyl]-1-oxobutyl]amino]methyl]cyclohexyl]carbonyl]-L-phenylalanine Phenylmethyl Ester To a solution of the monoacid obtained as disclosed at point E) of EXAMPLE 7 (0.9 g; 1.075 mol) in CH$_2$C$_2$ (15 mL) is added HATU (O-(7-Azabenzotriazol-1-yl)-N,N,N',N'-tetramethyluronium hexafluorophosphate) (0.475 g; 1.25 mol) and the mixture is stirred at 0° C. for 10 min. Diisopropylethylamine 0.39 g (3.0 mol) is then added and the mixture is stirred at 0° C. for ether 10 min. aB.-TFA salt [4-Phenyl-N-[[trans-4-(aminomethyl)cyclohexyl]carbonyl]-L-phenylalanine phenylmethyl ester] (0.584 g; 1.0 mol) (the amino compound 7) is then added to the reaction mixture and stirred at 0° C. for 2 h and at room temperature for 24 h. CH$_2$Cl$_2$ is removed and the residue is extracted with EtOAc (75.0 mL). The EtOAc solution is washed with K$_2$CO$_3$ solution (10%, 2×50 mL), water, and dried (Na$_2$SO$_4$). Evaporation of EtOAc gives an oil which is dried under vacuum to give a foamy solid, which is purified by silica gel column chromatography using EtOAc. Product containing fractions are collected and evaporated to give an oil, which is dried under vacuum to give foamy solid (1.1 g). This is found to be analytically pure and used in the next step.

Yield: 85%; Elemental analysis;

|  | C | H | N |
|---|---|---|---|
| % calc.: | 65.10 | 8.40 | 5.40 |
| % found: | 64.55 | 7.86 | 5.31 |

$^1$H-NMR, $^{13}$C-NMR, IR and MS spectra are consistent with the indicated structure.

B) 4-Phenyl-N-[[trans-4-[[[4-[bis[2-[bis[2-(1,1-dimethylethoxy)-2-oxoethyl]amino]ethyl]amino]-4-bis[1,1-dimethylethoxy)phosphinyl]-1-oxobutyl]amino]methyl]cyclohexyl]carbonyl]-L-phenylalanine To a solution of the benzylester obtained as disclosed at point A) (1 g; 0.0078 mol), is added 10% Pd-C (0.5 g; Degussa type, almost 50% water) and the mixture is hydrogenated at 45 psi for 8 h. The catalyst is filtered through Celite® and the filter cake is washed with THF (2×30 mL). The combined THF solution is concentrated on a rotary evaporator to give the acid as a thick viscous oil. This is dried under vacuum for 24 h to give a foamy solid (0.9 g) subsequently used as such without further purification.

Yield: 97%; $^1$H-NMR, $^{13}$C-NMR, IR and MS spectra are consistent with the indicated structure.

C) 4-Phenyl-N-[[trans-4-[[[4-[bis[2-[bis(carboxymethyl)amino]ethyl]amino]-1-oxo-4-phosphonobutyl]amino]methyl]cyclohexyl]carbonyl]-L-phenylalanine Trifluoroacetic acid (4 mL) is added to the hexa-(tert-butyl) ester (0.9 g; 0.75 mol) prepared at point B) and the mixture is stirred at room temperature for 12 h. Diethylether (30.0 mL) is then added to the reaction mixture and the precipitate is filtered and dried under vacuum to give a white solid (0.8 g) (Yield: 97%). HPLC analysis; of the TFA salt indicates that it is, fairly pure and useful for Gd chelation without further purification. An analytical sample is obtained from TFA salt (100 mg) by preparative HPLC. Fractions containing the pure product are collected and freeze dried to give a white fluffy solid (50 mg).

Purification yield: 50%; Elemental analysis; (calcd. for $C_{41}H_{55}F_3N_5O_{17}P \cdot 2H_2O$);

|  | C | H | N |
|---|---|---|---|
| % calc.: | 48.81 | 6.05 | 6.84 |
| % found: | 48.60 | 5.90 | 6.90 |

$^1$H-NMR, $^{13}$C-NMR, $^{31}$p-NMR IR and MS spectra are consistent with the indicated structure.

D) Gadolinium Complex of 4-Phenyl-N-[trans-4-[[[4-[bis[2-[bis(carboxymethyl)amino]ethyl]amino]-1-oxo-4-phosphonobutyl]amino]methyl]cyclohexylcarbonyl]-L-phenylalanine TFA salt obtained as disclosed at point C (0.3 g; 0.275 mol) is added to a mixture of acetonitrile (7.0 mL) and water (2 mL). To this a solution of Gd(OAc)$_3$ (0.132 g; 0.325 mol) in water (2.0 mL) is added dropwise. The initial pH of the solution is found to be 1.29. The solution becomes turbid and the pH of the solution is adjusted to 5.0 by adding a solution of meglumine in water. The turbid reaction mixture is stirred at room temperature for 48 h. The pH of the reaction mixture is then raised to 9.0 by the addition of meglumine solution and then purified by preparative HPLC using acetonitrile and water. Fractions containing the pure product were collected and freeze dried to give a fluffy solid (220 mg).

Yield: 78.5%; HPLC assay: 97.7% (in % area); Elemental analysis; for $C_{67}H_{119}N_9O_{35\ PGd}.5H_2O$;

|  | C | H | N | Gd |
|---|---|---|---|---|
| % calc.: | 42.60 | 6.88 | 6.67 | 8.32 |
| % found: | 42.54 | 6.93 | 6.47 | 7.06 |

IR and MS spectra are consistent with the indicated structure.

EXAMPLE 9

Gadolinium Complex of (3β,5β,7α,12α)-3-[[4-bis[2-[bis(Carboxymethyl)amino]ethyl]amino]-1-oxo-4-phosphonobutyl]amino]-7,12-dihydroxycholan-24-oic Acid, Salified with Sodium (1:4)

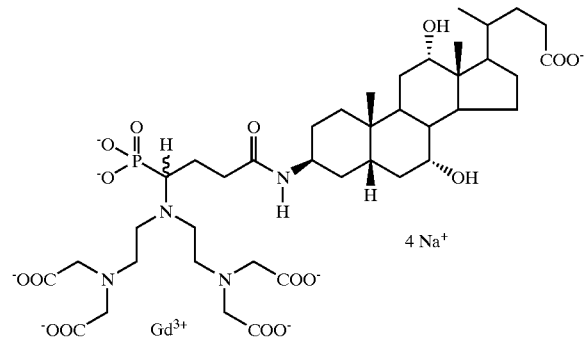

A) (3α,5β,7α,12α)-3-[4-[bis[2-[bis[2-(1,1-Dimethylethoxy)-2-oxoethyl]amino]ethyl]amino]-4-[bis[(1,1-dimethylethoxy)phosphinyl]-1-oxobutyl]amino]-7,12-dihydroxycholan-24-oic Acid Methyl Ester To a solution of the monoacid obtained as disclosed at point E) of EXAMPLE 7 (1.2 g; 1.4 mol) in $CH_2Cl_2$ is added HATU (0.6 g; 1.5 mol) and the mixture is stirred at 0° C. for 10 min. Diisopropylethylamine (1 mL) is then added and the mixture is stirred at 0° C. for her 10 min. 3β-Aminocholic acid methyl ester (compound disclosed in WO 9532741) (0.526 g; 1.25 mol) is then added to the mixture and stirred at 0° C. for 2 h and at room temperature for 48 h. $CH_2Cl_2$ is removed on a rotary evaporator and the residue is extracted with EtOAc. The EtOAc layer is washed with $K_2CO_3$ (10%, 2×30 mL), water and dried ($Na_2SO_4$). Evaporation of the EtOAc gives an oil which is purified by silica gel column chromatography ($CH_2Cl_2:CH_3OH$, 95:5). Product containing fractions (Rf=0.5,) are collected and evaporated to give an oil which is dried under vacuum to give the desire compound (1.1 g) as a foamy solid.

Yield 71%. TLC: Carrier: silica gel plate 60F 254 Merck; Eluent: $CH_2Cl_2$: $CH_3OH$ 95:5; Detection: $I_2$, 254 nm Rf=0.5; $^1$H-NMR, $^{13}$C-NMR, IR and MS spectra are consistent with the indicated structure.

B) (3α,5β,7α,12α)-3-[[[bis[2-[bis(2-(1,1-Dimethylethoxy)-2-oxoethyl]amino]ethyl]amino]-4-[bis(1,1-dimethylethoxy)phosphinyl]-1-oxobutyl]amino]-7,12-bis(acetyloxy)cholan-24-oic Acid Methyl Ester To a mixture of pyridine and acetic anhydride (1:1,2 mL) is added the dihydroxy cholic acid derivative prepared at step A) (1.24 g; 1 mol) and the mixture is stirred at room temperature for 48 h. Excess acetic anhydride and pyridine are removed and the residue is treated with a saturated solution of sodium bicarbonate (5.0 mL) and extracted with diethylether. The diethylether solution is washed with water and dried ($Na_2SO_4$). Evaporation of diethylether give a viscous oil which is purified by silica gel column chromatography using EtOAc-hexane (8:2). Fractions containing the product are collected and evaporated to give an oil which is dried under vacuum to give the desired diacetate (0.44 g) as a foamy solid.

Yield 75%. $^1$H-NMR, $^{13}$C-NMR, IR and MS spectra are consistent with the indicated structure.

C) (3α,5β,7α,12α)-3-[[4-[bis[2-[bis(Carboxymethyl)amino]ethyl]amino]-1-oxo-4-phosphonobutyl]amino]-7,12-dihydroxycholan-24-oic Acid Trifluoroacetic acid (3 mL) is added to the hexa (tert-butyl) ester prepared at step B) (0.662 g; 0.5 mol) and the mixture is stirred at room temperature for 30 min and kept at 4° C. for 18 h. Trifluoroacetic acid is then removed to give the desired deprotected intermediate (0.52 g) as an oil which is dried under vacuum. To a solution of said compound in ethanol water (1:1,5 mL) is added sodium hydroxide (20%, 5 mL) and the mixture is stirred at room temperature for 24 h. The completion of the reaction is followed by HPLC. The solvents are removed and the residue is neutralized with 1N HCl to give the completely deprotected polyacid as hydrochloride, which is filtered and dried under vacuum to give the desired chelating compound (0.35 g).

Yield: 79%. HPLC assay: 98% (in % area); $^1$H-NMR, $^{13}$C-NMR, IR and MS spectra are consistent with the indicated structure.

D) Gadolinium Complex of (3β,5β,7α,12α)-3-[[4-[bis[2-[bis(Carboxymethyl)amino]ethyl]amino]-1-oxo-4-phosphonobutyl]amino]-7,12-dihydroxycholan-24-oic Acid, Salified with Sodium (1:4)

To a solution of the $GdCl_3.6H_2O$ (50 mg, 0.135 mol) in water (2 mL) is added the hydrochloride prepared at step C) (0.104 g; 0.1 mol) dissolved in a mixture of acetonitrile-water (1:1; 7 mL). The initial pH of the reaction mixture is found to be 1.27. The pH of the reaction mixture is raised to 5.5 by the addition of 1N NaOH. The turbid reaction mixture is stirred for 48 h and the pH of the solution is raised 10 by the addition of 1N NaOH. The turbid solution obtained is centrifuged, the clear supernatant solution is collected and purified by preparative HPLC. Fractions containing the pure product are collected and freeze dried to give the desired compound.

Yield: 62%. HPLC assay: 98% (in % area); Elemental Analysis: (for $C_{40}H_{60}N_4O_{16}PGd.4Na.\ 8.H_2O$);

|  | C | H | Gd | N |
|---|---|---|---|---|
| % calc.: | 37.62 | 6.00 | 12.31 | 4.39 |
| % found.: | 37.37 | 5.95 | 11.43 | 4.40 |

MS: (M+H)$^+$=1046.4; IR spectrum is consistent with the indicated structure.

What is claimed is:

1. A compound having the formula (I), in the racemic or in the optically active form,

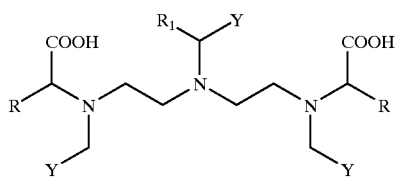

or a pharmaceutically acceptable salt thereof
wherein:

each Y group is independently a COOH group or a PO(OH)$_2$ group, with the proviso that at least one Y group is =PO(OH)$_2$, R is a hydrogen atom, or —(CH$_2$)$_m$—O—R$_2$, (C$_1$–C$_5$)-alkyl-(C$_6$–C$_{10}$)-aryl or (C$_1$–C$_5$)-alkyl-heteroaryl whose aryl or heteroaryl moiety comprises 1 or 2 fused rings optionally substituted with one or more halogen atoms, OH groups, (C$_1$–C$_5$)alkyl groups and/or an OR$_3$ group, wherein R$_2$ is (C$_1$–C$_5$)-alkyl-(C$_6$–C$_{10}$)-aryl, optionally substituted with one or more halogen atoms, OH and (C$_1$–C$_5$)-alkyl groups;

R$_3$ is (C$_6$–C$_{10}$) aryl optionally substituted with one or more halogen atoms, OH and/or (C$_1$–C$_5$)-alkyl groups;

m ranges from 1 to 5;

R$_1$ can have the same meanings as R with the proviso that when the Y group attached to the same carbon atom as R$_1$ is PO(OH)$_2$, R$_1$ is selected from H, (CH$_2$)$_m$NH$_2$, or (CH$_2$)$_m$COOH or an amido derivative thereof, and with the proviso that when at least two of the three Y groups are PO(OH)$_2$, the two R groups and R$_1$ cannot be contemporaneously H.

2. A compound as claimed in claim 1 wherein R is (C$_1$–C$_5$)-alkyl-(C$_6$–C$_{10}$)-aryl or a group —(CH$_2$)$_m$—O—R$_2$ wherein m ranges from 1 to 5 and R$_2$ is (C$_1$–C$_5$)-alkyl-(C$_6$–C$_{10}$)-aryl, the group (C$_1$–C$_5$)-alkyl-(C$_6$–C$_{10}$)-aryl consisting of benzyl, phenylethyl, and naphthylmethyl, wherein the aryl moiety is optionally substituted with one or more halogen atoms or OR$_3$ groups wherein R$_3$ is as defined in claim 1.

3. A compound as claimed in claim 1 wherein R is a (C$_1$–C$_5$)-alkyl-heteroaryl selected from pyridylmethyl or indolylmethyl.

4. A compound of claim 1, having formula (II)

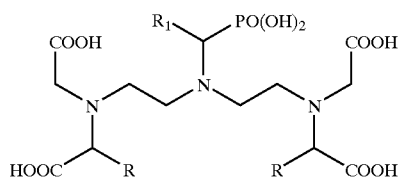

wherein R and R$_1$ are as defined in claim 1.

5. A compound as claimed in claim 1, having formula (III)

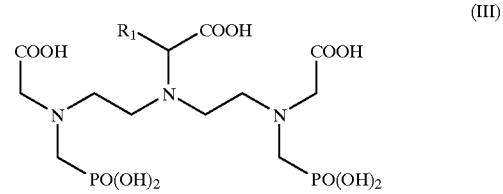

wherein R$_1$ is —(CH$_2$)$_m$—O—R$_2$, (C$_1$–C$_5$)-alkyl-(C$_6$–C$_{10}$)-aryl or (C$_1$–C$_5$)-alkyl-heteroaryl whose aryl or heteroaryl moiety comprises 1 or 2 fused rings optionally substituted with one or more halogen atoms, OH groups, alkyl(C$_1$–C$_5$) groups and/or an OR$_3$ group, wherein R$_2$ is (C$_1$–C$_5$)-alkyl-(C$_6$–C$_{10}$)-aryl, optionally substituted with one or more halogen atoms, OH and (C$_1$–C$_5$)-alkyl groups;

R$_3$ is (C$_6$–C$_{10}$) aryl optionally substituted with one or more halogen atoms, OH and/or (C$_1$–C$_5$)-alkyl groups; and m ranges from 1 to 5.

6. A compound as claimed in claim 1, having formula (IV),

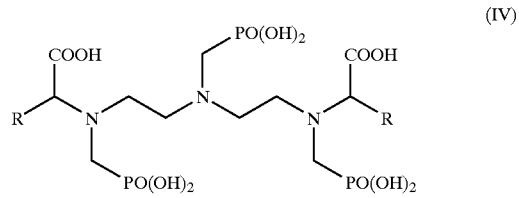

wherein R is as defined in claim 1, with the proviso that at least one of the two R groups is not H.

7. A compound as claimed in claim 1 selected from the group consisting of:

N,N'-[(Phosphonomethylimino)di-2,1-ethanediyl]bis[N-carboxymethyl-L-phenylalanine];

[4S-(4R*,1 2R*)]-4-carboxy-5,11-bis(carboxymethyl)-1-phenyl-12-[(phenyl-methoxy)methyl]-8-(phosphonomethyl)-2-oxa-5,8,11-triazatridecan-13-oic acid;

N,N'-[(Phosphonomethylimino)di-2,1-ethanediyl]bis[N-carboxymethyl-L-tryptophan];

N,N-Bis[2-[(carboxymethyl)(phosphonomethyl)amino]ethyl]-O-(4-hydroxy-phenyl)-3,5-diiodo-L-tyrosine;

N,N'-[(Phosphonomethylimino)di-2,1-ethanediyl]bis[N-(carboxymethyl)-glycine];

N,N'-[[[3-Carboxy-1-phosphonopropyl]imino]di-2,1-ethanediyl]bis[N-(carboxymethyl)glycine];

4-Phenyl-N-[trans-4-[[[4-[bis[2-[bis(carboxymethyl)amino]ethyl]-amino]-1-oxo-4-phosphonobutyl]amino]methyl]cyclohexylcarbonyl]-DL-phenylalanine;

(3β,5β,7α,12α)-3-[[4-[bis[2-[bis(carboxymethyl)amino]ethyl]amino]-1-oxo-4-phosphonobutyl]amino]-7,12-dihydroxycholan-24-oic acid; and N,N'-[[[3-Amino-1-phosphonopropyl]imino]di-2,1-ethanediyl]bis[N-carboxymethyl)glycine].

8. A complex comprising an ion of a metal element having atomic number of 20 to 31, 42, 43, 44, 49, 57 to 78 or 80 to 83, and a metal chelating ligand of formula (I),

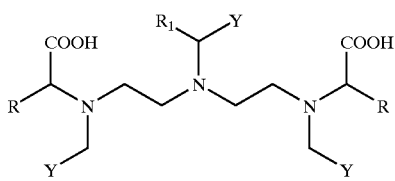
(I)

or a pharmaceutically acceptable salt thereof
wherein
  each Y group is independently a COOH group or a PO(OH)$_2$ group, with the proviso that at least one Y group is =PO(OH)$_2$,
  R is a hydrogen atom, or —(CH$_2$)$_m$—O—R$_2$, (C$_1$–C$_5$)-alkyl-(C$_6$–C$_{10}$)-aryl or (C$_1$–C$_5$)-alkyl-heteroaryl whose aryl or heteroaryl moiety comprises 1 or 2 fused rings optionally substituted with one or more halogen atoms, OH groups, alkyl(C$_1$–C$_5$) groups and/or an OR$_3$ group, wherein
    R$_2$ is (C$_1$–C$_5$)-alkyl-(C$_6$–C$_{10}$)-aryl, optionally substituted with one or more halogen atoms, OH and (C$_1$–C$_5$)-alkyl groups;
    R$_3$ is (C$_6$–C$_{10}$) aryl optionally substituted with one or more halogen atoms, OH and/or (C$_1$–C$_5$)-alkyl groups;
    m ranges from 1 to 5; and
    R$_1$ can have the same meanings as R with the proviso that when the Y group attached to the same carbon atom as R$_1$ is PO(OH)$_2$; R$_1$ is selected from H, (CH$_2$)$_m$NH$_2$, or (CH$_2$)$_m$COOH or an amido derivative thereof.

9. A complex as claimed in claim 8 wherein R is (C$_1$–C$_5$)-alkyl-(C$_6$–C$_{10}$)-aryl or a group —(CH$_2$)$_m$—O—R$_2$ wherein m ranges from 1 to 5 and R$_2$ is (C$_1$–C$_5$)-alkyl-(C$_6$–C$_{10}$)-aryl, the group (C$_1$–C$_5$)-alkyl-(C$_6$–C$_{10}$)-aryl consisting of benzyl, phenylethyl, or naphthylmethyl, wherein the aryl moiety is optionally substituted with one or more halogen atoms or OR$_3$ groups wherein R$_3$ is as defined in claim 8.

10. A complex as claimed in claim 8 wherein R is a (C$_1$–C$_5$)-alkyl-heteroaryl selected from pyridylmethyl or indolylmethyl.

11. A complex as claimed in claim 8, wherein the metal chelating ligand has formula (II)

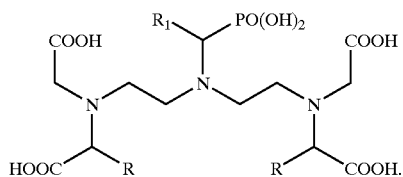
(II)

12. A complex as claimed in claim 8, wherein the metal chelating ligand has the formula (III)

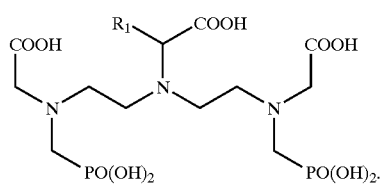
(III)

13. A complex as claimed in claim 8, wherein the metal chelating ligand has the formula (IV)

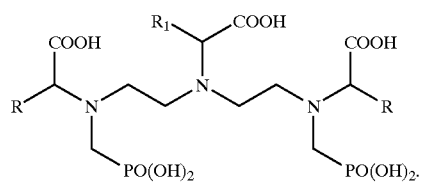
(IV)

14. A complex as claimed in claim 8, wherein the metal chelating ligand is selected from the group consisting of:
  N,N'-[(Phosphonomethylimino)di-2,1-ethanediyl]bis[N-carboxymethyl-L-phenylalanine];
  4S-(4R*,12R*)]-4-carboxy-5,11-bis(carboxymethyl)-1-phenyl-12-[(phenyl-methoxy)methyl]-8-(phosphonomethyl)-2-oxa-5,8,11-triazatridecan-13-oic acid;
  N,N'-[(Phosphonomethylimino)di-2,1-ethanediyl]bis[N-carboxymethyl-L-trypthophan];
  N,N-Bis[2-[(carboxymethyl)(phosphonomethyl)amino]ethyl]-O-(4-hydroxy-phenyl)-3,5-diiodo-L-tyrosine;
  N,N'-[(Phosphonomethylimino)di-2,1-ethanediyl]bis[N-(carboxymethyl)-glycine];
  N,N'-[(Phosphonomethylimino)di-2,1-ethanediyl]bis[N-(phosphonomethyl)-glycine];
  N,N'-[[[3-Carboxy-1-phosphonopropyl]imino]di-2,7-ethanediyl]bis[N-(carboxymethyl)glycine];
  4-Phenyl-N-[trans-4-[[[4-[bis[2-[bis(carboxymethyl)amino]ethyl]amino]-1-oxo-4-phosphonobutyl]amino]methyl]cyclohexylcarbonyl]-DL-phenylalanine;
  (3β,5β,7α,12α)-3-[[4-[bis[2-[bis(carboxymethyl)amino]ethyl]amino]-1-oxo-4-phosphonobutyl]amino]-7,12-dihydroxycholan-24-oic acid; and
  N,N'-[[[3-Amino-1-phosphonopropyl]imino]di-2,1-ethanediyl]bis[N-(carboxymethyl)glycine].

15. A complex as claimed in claim 8, wherein the metal ion is selected from the group consisting of Gd$^{(3+)}$, Dy$^{(3+)}$, Fe$^{(2+)}$, Fe$^{(3+)}$, and Mn$^{(2+)}$.

16. A complex as claimed in claim 8 having a $\tau_M$ value <100 ns.

17. A complex as claimed in claim 16 having a $\tau_M$ value between 10 and 100 ns.

18. A complex as claimed in claim 17 having a $\tau_M$ value between 20 and 50 ns.

19. A pharmaceutically acceptable salt according to claim 8 comprising a physiologically acceptable base selected from the group consisting of organic bases selected from primary, secondary, tertiary amines, basic amino acids, and inorganic bases with cations selected from sodium, potassium, magnesium, calcium or mixtures thereof.

20. A pharmaceutically acceptable salt according to claim 19, wherein the organic base is selected from the group consisting of ethanol amine, diethanolamine, morpholine, glucamine, N,N-dimethylglucamine, N-methylglucamine, lysine, arginine and ornithine.

21. A process for the preparation of a compound of claim 4, having the formula (II) wherein R$_1$ is H, which comprises:
  a) esterification of a suitable amino acid;
  b) N-alkylation of the ester from step a) by reacting it with a bromoacetate;
  c) bromoalkylation of the intermediate from step b) by reacting it with trifluoromethanesulfonic acid 2-bromoethyl ester prepared from bromoethanol, trifluoromethanesulfonic anhydride and 2,6-lutidine;

d) preparation of aminomethylphosphonic acid diethyl ester by direct condensation of tribenzylhexahydrotriazine with a dialkyl phosphite and subsequent debenzylation by catalytic hydrogenation of the condensation product;

e) bis alkylation of aminomethylphosphonic acid diethyl ester by reacting it with the intermediate from step c) and isolation of the hexaester; and f) deprotection of the acidic functions of the hexaester and isolation of the acid chelating agent.

22. A process according to claim 21 wherein the bromoalkyl derivative from step c) is prepared starting from the corresponding hydroxy derivative by reacting it with a suitable brominating agent.

23. A process for the preparation of a compound of claim 4, having the formula (II) wherein R is H, and $R_1$ has the meanings defined above in claim 4, which comprises:

a) preparation of 2,2'-iminodi-2,1-ethanediyl)bis-1H-isoindole-1,3(2H)-dione) by reacting phthalic anhydride with diethylenetriamine in acetic acid;

b) N-alkylation of the bis-phthalimido intermediate from step a) by reacting it with 3-benzyloxycarbonylpropionaldehyde in an organic medium, and by subsequent addition of tris(tert-butyl) phosphite;

c) removal of phthalic groups;

d) N-alkylation of the diamine from step c) by reacting it with a halo acetate;

e) debenzylation by catalytic hydrogenation of intermediate from d) and isolation of the hexaester monocarboxylic acid derivative;

f) reaction of the debenzylation intermediate from e) with an amino compound and isolation of the corresponding amide; and g) deprotection of the acidic functions of the hexaester and recovery of the acid chelating agent.

24. A process for the preparation of a compound of claim 5, having the formula (III), which comprises:

a) preparation of aminomethylphosphonic acid bis tert-butyl ester bis N-alkyl derivative by reacting an activated bis tert-butyl phosphite with aminal and directly transforming the resulting trimethylsilyl derivative into the corresponding hydroxy derivative by treatment with an aqueous acid;

b) catalytic hydrogenation of the intermediate from step a);

c) N-alkylation of the resulting compound from step b) by reacting it with a haloacetate;

d) transformation of the aminoalcohol from step c) into the corresponding bromo derivative by reacting it with methanesulfonyl chloride and a suitable brominating agent;

e) condensation of the bromo derivative from step d) with an esterified amino acid and recovery of the polyester; and f) deprotection of the acidic functions of the polyester and recovery of the chelating agent.

25. A process according to claim 24 wherein in step a) the phosphonic acid tert-butyl ester is activated with $Me_3SiCl$.

26. A process according to claim 24 wherein the synthesis of the aminomethylphosphonic acid bis tert-butyl ester bis N-alkyl derivative in step a) is catalyzed by a catalytic amount of a lanthanide triflate.

27. A process according to claim 26 wherein the lanthanide triflate is ytterbium triflate.

28. A pharmaceutical diagnostic composition comprising a chelated complex of claim 8 in admixture with a suitable carrier.

29. A contrast agent comprising a complex of claim 8.

30. A method of imaging human or animal body organs or tissues comprising administering a complex of claim 8 and imaging said organs or tissues by magnetic resonance imaging.

\* \* \* \* \*